United States Patent
Ouyang et al.

(10) Patent No.: US 9,427,469 B2
(45) Date of Patent: Aug. 30, 2016

(54) SOLUBLE PHYSIOLOGICAL CHITOSAN FORMULATIONS COMBINED WITH PLATELET-RICH PLASMA (PRP) FOR TISSUE REPAIR

(75) Inventors: Wei Ouyang, Montreal (CA); Michael Buschmann, Montreal (CA); Anik Chevrier, Pointe-Claire (CA)

(73) Assignee: ORTHO REGENERATIVE TECHNOLOGIES INC., Quebec (CA)

( * ) Notice: Subject to any disclaimer, the term of this patent is extended or adjusted under 35 U.S.C. 154(b) by 0 days.

(21) Appl. No.: 13/510,663

(22) PCT Filed: Nov. 19, 2010

(86) PCT No.: PCT/CA2010/001858
§ 371 (c)(1),
(2), (4) Date: Sep. 4, 2012

(87) PCT Pub. No.: WO2011/060555
PCT Pub. Date: May 26, 2011

(65) Prior Publication Data
US 2013/0004474 A1   Jan. 3, 2013

Related U.S. Application Data

(60) Provisional application No. 61/262,792, filed on Nov. 19, 2009.

(51) Int. Cl.
| | | |
|---|---|---|
| *A01N 63/00* | (2006.01) |
| *A01N 65/00* | (2009.01) |
| *A61K 45/06* | (2006.01) |
| *A61K 31/722* | (2006.01) |
| *A61K 33/14* | (2006.01) |
| *A61K 35/16* | (2015.01) |
| *A61L 27/20* | (2006.01) |
| *A61L 27/36* | (2006.01) |
| *C08L 5/08* | (2006.01) |
| *C08K 3/16* | (2006.01) |
| *C08K 5/521* | (2006.01) |

(52) U.S. Cl.
CPC ............ *A61K 45/06* (2013.01); *A61K 31/722* (2013.01); *A61K 33/14* (2013.01); *A61K 35/16* (2013.01); *A61L 27/20* (2013.01); *A61L 27/3616* (2013.01); *C08L 5/08* (2013.01); *C08K 3/16* (2013.01); *C08K 5/521* (2013.01)

(58) Field of Classification Search
None
See application file for complete search history.

(56) References Cited

U.S. PATENT DOCUMENTS

| | | | | |
|---|---|---|---|---|
| 5,510,102 A | * | 4/1996 | Cochrum | 424/78.08 |
| 5,614,204 A | * | 3/1997 | Cochrum | 424/423 |
| 5,885,609 A | * | 3/1999 | Amiji | 424/425 |
| 6,322,785 B1 | * | 11/2001 | Landesberg et al. | 424/93.72 |
| 6,624,245 B2 | * | 9/2003 | Wallace et al. | 525/54.1 |
| 2002/0165337 A1 | * | 11/2002 | Wallace et al. | 528/373 |
| 2002/0197302 A1 | * | 12/2002 | Cochrum et al. | 424/445 |
| 2003/0007957 A1 | * | 1/2003 | Britton et al. | 424/93.72 |
| 2003/0152639 A1 | * | 8/2003 | Britton et al. | 424/529 |
| 2004/0078077 A1 | * | 4/2004 | Binette et al. | 623/13.17 |
| 2004/0078090 A1 | * | 4/2004 | Binette et al. | 623/23.76 |
| 2004/0208845 A1 | * | 10/2004 | Michal et al. | 424/78.24 |
| 2005/0125077 A1 | * | 6/2005 | Harmon et al. | 623/23.72 |
| 2005/0226916 A1 | * | 10/2005 | Cochrum et al. | 424/445 |
| 2007/0053957 A1 | * | 3/2007 | Kennedy et al. | 424/443 |
| 2009/0148486 A1 | * | 6/2009 | Lu et al. | 424/422 |
| 2013/0004474 A1 | * | 1/2013 | Ouyang et al. | 424/93.72 |

FOREIGN PATENT DOCUMENTS

| | | |
|---|---|---|
| WO | WO 96/23039 | 8/1996 |
| WO | WO 99/07416 | 2/1999 |
| WO | WO 2006/015178 | 2/2006 |
| WO | WO2008/064487 | 6/2008 |

OTHER PUBLICATIONS

Rinaudo et al (Polymer, 40:7029-7032 (1999).*
Hoemann et al., The Journal of Bone and Joint Surgery, 87:2671-2686 (2005). "Chitosan-glycerol phosphate/blood implants improve hyaline cartilage repair in ovine microfracture defects."
Akeda, K. et al., Osteoarthritis and Cartilage,14:1272-1280 (2006). "Platelet-rich plasma stimulates porcine articular chondrocyte proliferation and matrix biosynthesis."
Casati, M.Z. et al., Int. J. Oral Maxillofac. Surg., 36:132-136 (2007). "Platelet-rich plasma does not improve bone regeneration around peri-implant bone defects—a pilot study in dogs."
Chenite, A. et al., Biomater., 21:2155-2161 (2000). "Novel injectable neutral solutions of chitosan form biodegradable gels in situ."
Chenite, A. et al., Carbohyd. Polym., 46:39-47 (2001). "Rheological characterization of thermogelling chitosan/glycerol-phosphate solutions."
Luengo Gimeno, F. et al., Thrombosis Journal, 4:18¬ 25 (2006). "Preparation of platelet-rich plasma as a tissue adhesive for experimental transplantation in rabbits."
Hoemann, C.D. et al., Osteoarthritis & Cartilage,15:78-89 (2007). "Chitosan-glycerol phosphate/blood implants elicit hyaline cartilage repair integrated with porous subchondral bone in microdrilled rabbit defects."
Mendonca-Caridad, J.J. et al., Int. J. Oral Maxillofac. Surg., 35:88-91 (2006). "Frontal sinus obliteration and craniofacial reconstruction with platelet rich plasma in a patient with fibrous dysplasia."
Ranly, D.M. et al., J. Bone Joint Surg. Am., 89:139-147 (2007). "Platelet-rich plasma inhibits demineralized bone matrix-induced bone formation in nude mice."

(Continued)

*Primary Examiner* — Thomas J Visone
(74) *Attorney, Agent, or Firm* — Eric L. Lane; Green Patent Law

(57) ABSTRACT

The present disclosure relates to an activated polymer composition for use in repairing tissue of a patient comprising platelet-rich plasma (PRP), a chitosan solution, a salt such as NaCl or glycerol phosphate, and an activator such as at least one of $CaCl_2$ and a mixture of thrombin/$CaCl_2$.

16 Claims, 11 Drawing Sheets

(56) References Cited

OTHER PUBLICATIONS

You, T.M. et al., Oral Surg. Oral Med. Oral Pathol. Oral Radiol. Endo., 103: e8-e12 (2007). "The effect of platelet-rich plasma on bone healing around implants placed in bone defects treated with Bio-Oss: a pilot study in the dog tibia."

Chang et al., Biomedical engineering—Applications, Basis and Communications, 21(2)115-122, (2009). "Evaluation of chitosan/CaS04/platelet-rich plasma microsphere composites as alveolus osteogenesis material".

Cheng et al., Tissue Engineering, 12(4):1018, (2006). "Effect of injectable scaffolds materials chitosan-beta-tricalcium phosphate with platelet-rich plasma on proliferation of bone marrow stromal cells in vitro", abstract #102.

Cheng et al., Zhonghua-Chuangshang-Guke-Zazhi= Chinese Journal of Orthopaedic Trauma, Chinese Medical Association, China, 10(12):1166-1170, (2008). "Effect of injectable chitosan-beta-tricalcium phosphate with platelet-rich plasma on bone regeneration in vivo" (English abstract only).

Shen et al., Clin. Oral Impl. Res., 17(5): 572-578, (2006). "Releasing growth factors from activated human platelets after chitosan stimulation: a possible bio-material for platelet-rich plasma preparation".

Chevrier et al., Osteoarthritis and Cartlige, 15(3):316-327, (2007). "Chitosan-glycerol phosphate/blood implants increase cell recruitment, transient vascularization and subchondral bone remodeling in drilled cartilage defects".

Marchand et al. Osteoarthritis and Cartilage, 17(7):953-960, (2009). "Solidification mechanisms of Chitosan-glycerol phosphate/blood implant for articular cartilage repair".

Oktay et al., The Journal of Oral Implantology, 36(3):175-184, (2010)., "Effects of platelet-rich plasma and chitosan combination on bone regeneration in experimental rabbit cranial defects".

Kutlu et al., Journal of Biomedical materials research, Part B. Applied Biomaterials, 101B(1):28-35, (2013). "Platelet-rich plasma-loaded chitosan scaffolds: Preparation and growth factor release kinetics".

Bi L et al., Biomaterials, 31(12):3201-3211, (2010)., "Reconstruction of goat tibial defects using an injectable tricalcium phosphate/chitosan in combination with autologous platelet-rich plasma".

* cited by examiner

SOLUBLE PHYSIOLOGICAL CHITOSAN FORMULATIONS COMBINED WITH PLATELET-RICH PLASMA (PRP) FOR TISSUE REPAIR

CROSS REFERENCE TO RELATED APPLICATIONS

This application is a 35 U.S.C. §371 National Phase Entry Application of International Application No. PCT/CA2010/001858 filed Nov. 19, 2010, which designates the U.S., and which claims benefit under 35 U.S.C. §119(e) of U.S. Provisional Application No. 61/262,792, filed Nov. 19, 2009, the contents of which are incorporated herein by reference in their entireties.

TECHNICAL FIELD

The present invention relates to soluble physiological chitosan formulations combined with platelet-rich plasma (PRP) for tissue repair, which includes both thrombin and/or $CaCl_2$ as clot activator and different mixing methods.

BACKGROUND ART

Chitosan is a linear polysaccharide composed of β-(1-4)-linked D-glucosamine (deacetylated unit) and N-acetyl-D-glucosamine (acetylated unit), which primarily results from the alkaline deacetylation of chitin. Chitosan can exist in many structural conformations, depending on a variety of factors that include the degree of hydration, the electrolyte environment and the complexity of original chitin mixture. Chitosan and its amino-substituted derivatives are bioerodible, biocompatible and biodegradable cationic polymers that have been advanced for a wide variety of applications, including tissue engineering, drug and gene delivery, pharmaceutical formulation, scaffolds for cell growth and cell encapsulation, wound healing and surface hemostasis.

A well known property of chitosan is its solubility at acidic pH (<6) and insolubility at neutral pH, making its use in solution with living cells and tissues problematic. Various publications (Chenite, international patent application publication No. WO 99/07416; Chenite et al., 2000, Biomater., 21: 2155-2161; Chenite et al., 2001, Carbohyd. Polym., 46: 39-47) describe that admixing a polyol-phosphate dibasic salt, i.e. glycerol-phosphate (GP), to an aqueous solution of chitosan can increase the pH of the solution while avoiding precipitation of the polymer. In the presence of these particular salts, chitosan solutions of substantial concentration (0.5-3%) and high molecular weight (>several hundred kDa) remain liquid, at low or room temperature, for a long period of time with physiologically acceptable neutral pH region between 6.8 and 7.2. These chitosan-glycerol phosphate solutions which can gel upon mild heating (for example from 4 to 37° C.), are biocompatible, biodegradable and adhesive to human tissues, provide for new opportunities in the delivery of sensitive therapeutics.

Chitosan's properties allow it to rapidly clot blood, and have recently gained approval in the USA for use in bandages and other hemostatic agents. The first step in the early wound healing process is hemostasis due to blood coagulation. One approach to improve healing is to stabilize the blood clot by dispersing a soluble biocompatible polymer throughout uncoagulated fresh blood, the polymer acting as a scaffold throughout the clot to maintain its volume and to increase clot adhesion to tissues at the lesion site (Iliescu et al., 2007, Microsc. Res. Tech., 71: 236-247). Chitosan-GP solutions are non-toxic and bioresorbable, in addition to permitting coagulation and impeding clot retraction. They are mixed with autologous blood to form viscous chitosan-GP/blood mixtures that solidified in about 10 minutes in part due to the thrombogenicity of chitosan (Hoemann et al., 2007, Osteoarthritis & Cartilage, 15: 78-89).

Platelet-rich plasma (PRP) is a blood-derived product that concentrates a high number of platelets in a small volume of plasma. It has a substantial role in tissue regeneration and wound healing. In some applications, platelets have been used directly without being formulated. In other applications, a platelet gel (also known as a platelet clot) has been used that was prepared from PRP. The term "platelet gel" was introduced to describe the gelatin-like malleable product that results when thrombin and calcium are added to PRP. The addition of thrombin and calcium induces the cleaving fibrinogen to form fibrin which polymerizes, producing a glue-like gel. Platelets trapped in the gel are activated and release bioactive molecules. In most studies and clinical applications for tissue repair, a thrombin/calcium chloride solution was used to activate platelets to make PRP form a platelet gel. For example: PRP was clotted by adding a 10% thrombin solution (v/v, 1000 U/ml in 100 mM $CaCl_2$) to yield a final thrombin concentration of 100 U/ml (Akeda et al., 2006, Osteoarthritis and Cartilage, 14: 1272-1280); 200 µl of PRP was treated with 20 µl of sterile bovine thrombin prepared by mixing 25 µl of the enzyme (1000 U/ml) in 10 ml of $CaCl_2$ under sterile conditions to obtain a clot (Ranly et al., 2007, J. Bone Joint Surg. Am., 89: 139-147). PRP has also been activated just before application with 10% calcium chloride solution and 5000 units of bovine thrombin to form a gel (You et al., 2007, Oral Surg. Med. Oral Oral Pathol. Oral Radiol. Endo., 103: e8-e12).

In a few studies and clinical applications, only calcium was used to activate platelets to make PRP form a platelet gel (clot). For example: 10% $CaCl_2$ solution was added into PRP to activate platelets and the platelet gel formed after 10 to 15 minutes (Casati et al., 2007, Int. J. Oral Maxillofac. Surg., 36: 132-136). Calcium chloride solutions with different concentration (5%, 10%, 25%, and 50%) have also been used alone to induce platelet activation, revealing that $CaCl_2$ alone was suitable for triggering PRP activation, and that 5% calcium chloride solution was the most effective concentration in activating PRP to clot (Fedrico Luengo Gimeno et al., 2006, Thrombosis Journal, 4:18-25). PRP clots were also prepared by adding 0.5 ml of 10% calcium chloride to tubes and mixing with PRP. The mixture was then clotted with bone graft material graft (Human Freeze Dried Demineralized Cortical Bone) (Mendonca et al., 2006, Int. J. Oral Maxillofac. Surg., 35: 88-91). International patent application publication No. WO 96/23039 describes a novel type of hemostatic adhesive agents. These agents were prepared from PRP concentrate in combination with physiologically acceptable biocompatible polymers, which included alginates, poly-L-amino acids (poly-L lysine, poly-L-histidine and poly-α-D-glutamic acid), chitosan and chitin. In the presence of calcium ions, the combination of plasma concentrate with the polymers formed adhesives which had very strong adhesive properties and very rapid onset of these adhesive properties.

There is still a need for an improved polymer formulation with an improved solubility at physiological pH and ionic strength that can be mixed with PRP to form a hybrid polymer/PRP implant. There is a specific need for a hybrid polymer/PRP implant with good mechanical properties that can be obtained by a simple preparation method.

SUMMARY

In accordance with the present disclosure, there is now provided a clot activating polymer composition for use in repairing tissue of a patient comprising platelet-rich plasma (PRP), a chitosan, a salt and a clot activator.

According to a first aspect, the present application provides a clot-activated polymer composition comprising platelet-rich plasma (PRP), a chitosan, a salt and a clot activator. In an embodiment, the salt may be an organic or inorganic salt. In an embodiment, the inorganic salt is sodium salt, chloride salt, potassium salt, calcium salt, magnesium salt, phosphate salt, sulfate salt and/or carboxylate salt. In another embodiment, the inorganic salt is at least one of NaCl, KCl, CsCl, $CaCl_2$, CsF, $KClO_4$ $NaNO_3$ and/or $CaSO_4$. In another embodiment, the organic salt is glycerolphosphate (such as βGP). In a further embodiment, the clot activator is a $CaCl_2$ solution (having, for example, a concentration equal to or higher than about 1.0% w/w and equal to or lower than about 25% w/w or equal to or higher than about 1.3% w/w and equal to or lower than about 3%) that can be optionally combined with thrombin. In still another embodiment, the polymer can prepared by combining said PRP to a chitosan solution comprising said chitosan and said salt at a volume ratio of equal to or lower than about 3:1 or about 2:1 v/v. In still another embodiment, the polymer can prepared by combining said PRP to a chitosan solution comprising said chitosan and said salt at a volume ratio equal to or lower than 4:1 and equal to or lower than 1:1. In an embodiment, the polymer composition has a pH equal to or higher than about 6.2 and equal to or lower than about 6.8. In still another embodiment, the polymer is prepared with a solution of said chitosan having an osmolality equal to or higher than about 250 mOsm/kg and equal to or lower than about 600 mOsm/kg or an osmolality equal to or higher than about 342 mOsm/kg and equal to or lower than about 361 mOsm/kg. In an embodiment, the polymer is prepared with a solution of said chitosan having a chitosan concentration of equal to or higher than about 1.0% w/w and equal to or lower than about 10% w/w or a chitosan concentration is equal to or higher than about 1.62% w/w and equal to and lower than about 2% w/w. In another embodiment, the chitosan has a degree of deacetylation (DDA) equal to or higher than about 20% and equal to or lower than about 100% (such as, for example, about 76% or about 81%). In another embodiment, the chitosan has a number average molecular weight ($M_n$) equal to or higher than about 1 kDa and equal to or lower than about 10 MDa (such as, for example, about 232 kDa or about 298 kDa). In still another embodiment, the polymer further comprises a mineral acid or an organic acid, including, but not limited to hydrochloric acid, acetic acid, nitric acid, phosphoric acid, sulfuric acid, boric acid hydrofluoric acid and/or hydrobromic acid.

According to a second aspect, the present application provides a clot-activated polymer composition prepared by combining platelet-rich plasma (PRP), a chitosan solution, a salt solution and a clot activator solution. In this polymer composition, the concentration of chitosan in said chitosan solution is equal to or higher than about 1.0% w/w and equal to or lower than about 10% w/w, and the volume ratio between the PRP and the chitosan solution is between about 4:1 to about 1:1. In an embodiment, the polymer composition can also be obtained by combining a mineral acid or an organic acid (such as, for example, mineral acid is hydrochloric acid, acetic acid, nitric acid, phosphoric acid, sulfuric acid, boric acid hydrofluoric acid and/or hydrobromic acid). In a further embodiment, the salt solution comprises an inorganic salt, including, but not limited to sodium salt, chloride salt, potassium salt, calcium salt, magnesium salt, phosphate salt, sulfate salt and/or carboxylate salt (such as, for example, NaCl, KCl, CsCl, $CaCl_2$, CsF, $KClO_4$, $NaNO_3$ and/or $CaSO_4$). In another embodiment, the salt solution comprises an organic salt, such as, for example, glycerolphosphate (or βGP). In still another embodiment, the clot activator solution comprises thrombin at a concentration from about 100 U/ml to about 1000 U/ml diluted in a 10% w/w of a $CaCl_2$ solution. In another embodiment, the clot activator is a $CaCl_2$ solution optionally combined with thrombin. In another embodiment, the volume ratio between a first solution comprising the PRP, the chitosan solution and the salt and a second solution comprising the clot activator is equal to or lower than about 10:1, or about 9:1. In another embodiment, the concentration of $CaCl_2$ in the $CaCl_2$ solution is equal to or higher than about 1.0% w/w and equal to or lower than about 25% w/w or equal to or higher than about 1.3% w/w and equal to or lower than about 3% w/w. In still another embodiment, the volume ratio of between the PRP and the chitosan solution is equal to or lower than about 3:1, about 2:1. In still another embodiment, the polymer composition has a pH equal to or higher than about 6.2 and equal to or lower than about 6.8. In a further embodiment, the chitosan solution has an osmolality equal to or higher than about 250 mOsm/kg and equal to or lower about 600 mOsm/kg or equal to or higher than about 342 mOsm/kg and equal to or lower than about 361 mOsm/kg. In still another embodiment, the concentration of chitosan in said chitosan solution is equal to or higher than about 1.62% w/w and equal to or lower than about 2% w/w. In still another embodiment, the chitosan of said chitosan solution has a degree of deacetylation (DDA) equal to or higher than about 20% and equal to or lower than about 100% (such as, for example, about 76% or about 81%). In still a further embodiment, the chitosan of the chitosan solution has a number average molecular weight ($M_n$) equal to or higher than about 1 kDa and equal to or lower than about 10 MDa (such as, for example, about 232 kDa or about 298 kDa).

In a third aspect, the present application provides a method for repairing a tissue of a patient, said method comprising the step of introducing into said tissue a clot-activated polymer composition as defined herein such that the composition adheres to the tissue and promotes cell proliferation for repairing the tissue. In an embodiment, the tissue is cartilage, meniscus, ligament, tendon, bone, skin, cornea, periodontal tissues, maxillofacial tissues, temporomandibular tissues, abscesses, resected tumors and/or ulcers.

In a fourth aspect, the present application provides use of a clot-activated polymer composition as defined herein for repairing a tissue of a subject, wherein the polymer composition adheres to the tissue and promotes cell proliferation as well as the use of a clot-activated polymer composition as defined herein in the manufacture of a medicament for repairing a tissue of a subject, wherein the polymer composition adheres to the tissue and promotes cell proliferation. In an embodiment, the tissue is cartilage, meniscus, ligament, tendon, bone, skin, cornea, periodontal tissues, maxillofacial tissues, temporomandibular tissues, abscesses, resected tumors and/or ulcers.

In a fifth aspect, the present application provides a method of preparing a clot-activated polymer composition for repairing tissue in a subject. Broadly, the method comprises dissolving from 1.0% w/w to 10.0% w/w of chitosan in HCl to provide a chitosan-HCl mixture, adding a NaCl solution or glycerol phosphate to the chitosan-HCl mixture to provide a chitosan-HCl-salt mixture, admixing platelet-rich plasma (PRP) to the chitosan-HCl-salt mixture at a volume ratio between about 4:1 and about 1:1 to provide a PRP/chitosan-HCl-salt mixture; and adding a clot activator to the PRP/chitosan-HCl-salt mixture at a volume ratio of between about 5:1 to about 10:1. In an embodiment, the clot activator is a $CaCl_2$ solution optionally combined with thrombin. In another embodiment, in step a), wherein the chitosan is dissolved in HCl by heating at a temperature of about 60° C. for about 2 hours. In still another embodiment, the chitosan is provided in a solution of about 1.62% w/w. In yet another embodiment, the chitosan has a degree of deacetylation (DDA) of about 76% or of about 81%. In yet another embodiment, the chitosan has a number average molecular weight ($M_n$) of about 232 kDa or of about 298 kDa. In yet a further embodiment, the hydrochloric acid is provided as a 38 mM solution or as a 71 mM solution. In an embodiment, the NaCl is provided as a 150 mM solution or as a 160 mM solution. In an embodiment, the β-glycerol phosphate is provided as a 2.15% w/w solution. In another embodiment, the concentration of $CaCl_2$ in the $CaCl_2$ solution is equal to or higher than about 1.0 w/w and equal to or lower than about 25% w/w. In yet another embodiment, the thrombin is provided as a solution of about 100 U/ml to about 1000 U/ml diluted with 10% w/w of the $CaCl_2$ solution. In still another embodiment, the clot activator is layered on top of the PRP/chitosan-HCl-salt mixture. In still another embodiment, the clot activator is gently mixed by inversion with the PRP/chitosan-HCl-salt mixture.

Accordingly, it is provided a clot-activated polymer composition comprising platelet-rich plasma (PRP), a chitosan solution, a salt and a clot activator.

In an embodiment, the salt is an organic or inorganic salt. The inorganic salt can be sodium salt, chloride salt, potassium salt, calcium salt, magnesium salt, phosphate salt, sulfate salt or carboxylate salt. Alternatively, the salt is at least one of NaCl, KCl, CsCl, $CaCl_2$, CsF, $KClO_4$ $NaNO_3$ or $CaSO_4$. Furthermore, the organic salt can be glycerol-phosphate.

In another embodiment, the activator is at least one of a $CaCl_2$ solution or a mixture of thrombin/$CaCl_2$.

In a further embodiment, the mix ratio of PRP/chitosan-salt and activator is at most 10:1, or at most 9:1 of a volume ratio.

In an additional embodiment, the concentration of the $CaCl_2$ activator is between 1.0% w/w to 25% w/w, alternatively between 1.3% w/w to 3% w/w.

In another embodiment, the mix ratio of PRP:chitosan is from 4:1 to 1:1 v/v, alternatively 3:1, or 2:1 v/v.

In an additional embodiment, the composition has a pH between 6.2 and 6.8.

In another embodiment, the chitosan solution has an osmolality between 250 mOsm/kg and 600 mOsm/kg, alternatively between 342 mOsm/kg and 361 mOsm/kg.

In a further embodiment, the concentration of chitosan in the chitosan solution is between about 1.0% w/w to 10% w/w more particularly between about 1.62% w/w to 2% w/w.

In another embodiment, the chitosan of said chitosan solution has a degree of deacetylation (DDA) between 20% to 100%, more particularly of 76% or 81%.

In another embodiment, the chitosan of the chitosan solution has a number average molecular weight ($M_n$) ranging from 1 kDa to 10 MDa, more particularly of 232 kDa or 298 kDa.

In a further embodiment, the composition described herein further comprises a mineral acid or an organic acid, such as for example hydrochloric acid, acetic acid, nitric acid, phosphoric acid, sulfuric acid, boric acid hydrofluoric acid or hydrobromic acid.

It is also provided herein a clot-activated polymer composition prepared by combining platelet-rich plasma (PRP), a chitosan solution, a salt and an activator; wherein the concentration of chitosan in the chitosan solution is between about 1.0% w/w to 10% w/w; and the PRP: chitosan ratio being 4:1 to 1:1 v/v.

In an embodiment, the activator is thrombin from 100 U/ml to 1000 U/ml diluted with 10% w/w of $CaCl_2$.

It is also provided a method for repairing a tissue of a patient, the method comprising the step of introducing into the tissue a polymer composition as defined in herein such that the composition adheres to the tissue and promotes cell proliferation for repairing the tissue.

In an embodiment, the tissue can be cartilage, meniscus, ligament, tendon, bone, skin, cornea, periodontal tissues, maxillofacial tissues, temporomandibular tissues, abscesses, resected tumors and/or ulcers.

It is also provided herein the use of a polymer composition as defined herein for repairing a tissue of a subject, and/or in the manufacture of a medicament for repairing a tissue of a subject, wherein the polymer composition adheres to the tissue and promotes cell proliferation.

It is additionally provided herein a method of preparing a polymer composition for repairing tissue in a subject, the method comprising the step of dissolving from 1.0% w/w to 10.0% w/w of chitosan in HCl; adding a NaCl solution or glycerol phosphate to the chitosan-HCl mixture; admixing platelet-rich plasma (PRP) to the chitosan-HCl—NaCl or chitosan-HCl-βGP mixture in a ratio between 4:1 and 1:1 v/v; and adding an activator to the PRP/chitosan-HCl—NaCl or glycerol phosphate mixture in a ratio of at most from 5:1 to 10:1 v/v.

In an embodiment, the chitosan is dissolved in HCl by heating at 60° C. for about 2 hours.

In another embodiment, the composition comprises 1.62% w/w of chitosan with a degree of deacetylation (DDA) of 76% or 81% with a number average molecular weight ($M_n$) of 232 kDa or 298 kDa, 38 mM or 71 mM of hydrochloric acid, and 150 mM or 160 mM of NaCl, or 2.15% w/w of β-glycerol phosphate.

In a further embodiment, the activator is layered on top of the PRP/chitosan-HCl—NaCl or chitosan-HCl-βGP mixture.

In another embodiment, the activator is gently mixed by inversion with the PRP/chitosan-HCl—NaCl or chitosan-HCl-βGP mixture.

BRIEF DESCRIPTION OF THE DRAWINGS

Reference will now be made to the accompanying drawings.

DETAILED DESCRIPTION

Figure 1:
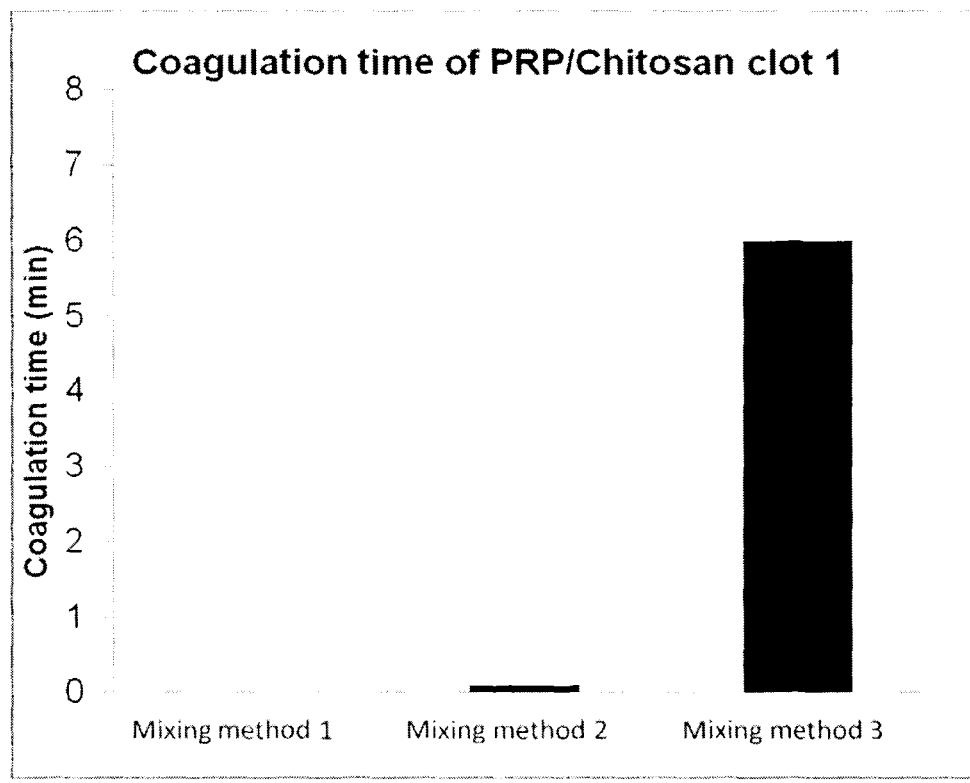
FIG. 1 is a histogram reflecting the coagulation time of PRP/chitosan clots-1 (PRP/chitosan-HCl—NaCl pH 6.6) prepared with thrombin/$CaCl_2$ activator by different mixing methods. Mixing method 1 was gentle inversion, mixing method 2 was drawing into a syringe without inversion and mixing method 3 was layering.

Is now provided and disclosed herein a novel formulation of PRP/chitosan mixtures activated by a clot activator (such as CaCl$_2$ and/or thrombin). Such formulations are useful for the facilitating tissue repair.

The clot-activated polymer compositions described herein are capable of allowing the formation of a platelet gel or clot. The other components of the polymer composition (such as chitosan, the salt and optionally the acid) allow the PRP to be activated with conventional methods using a clot activator (such as CaCl$_2$ and/or thrombin) to form a platelet gel (or platelet clot). The clot-activated polymer compositions described herein are capable of allowing the formation of a paste-like or gel. For example, and as shown below, the PRP included in the composition does enable the formation of a chitosan-based gel.

The clot-activated polymer compositions described herein comprise a PRP, a chitosan, a salt and a clot activator. In an embodiment, the clot-activated compositions described herein solely contain plasma rich in platelets as blood-derived products. In another embodiment, the PRP is autologous with respect to the recipient of the compositions, i.e. the PRP is obtained from the same individual who is going to receive the clot-activated polymer composition. However, the PRP can also be allogeneic to the recipient, i.e. obtained from an individual that is immunologically distinct from the recipient of the clot-activated polymer composition but where the individual and the recipient are from the same species. In this embodiment, the PRP should be preferably matched (in part or in total) with at least one or several platelet antigens. In another embodiment, the PRP can also be xenogeneic to the recipient, i.e. obtained from an individual that is immunologically distinct from the recipient of the clot-activated polymer composition and where the individual and the recipient are not from the same species. In still a further embodiment, the PRP can be derived from a human source.

As used herein, the clot activator is an agent capable of inducing clotting of PRP and the formation of a platelet gel from a native PRP. Such clot activators include, but are not limited to a CaCl$_2$ solution and a combination of CaCl$_2$ and thrombin.

In an embodiment, the clot-activated polymer consists essentially of a PRP, a chitosan, a salt and a clot activator. In this specific embodiment, other active agents which are participating to the formation of the gel or clot are not included. However, other components such as an acid (to facilitate the dissolution of the chitosan), preservatives or medicines can be included.

As defined herein as method 1, thrombin with the concentration of 1000 U/ml (thrombin was dissolved in 10% w/w $CaCl_2$ solution) was used to activate the PRP/chitosan mixtures, and the mix ratio of PRP/chitosan mixture to thrombin/$CaCl_2$ solution is 9:1 at volume ratio.

Another aspect identified as mixing method 1, is the formation of PRP/chitosan mixtures, where thrombin/$CaCl_2$ was mixed into PRP/chitosan by 5 times gentle inversion of the mixing tube containing stainless steel beads and then drawn into a syringe for placement in glass tubes for preparing clot (implant).

Still another aspect is to provide a novel method identified as mixing method 2 of formation of PRP/chitosan mixtures, where thrombin/$CaCl_2$ was added to the PRP/chitosan without inversion and directly drawn into a syringe for placement in glass tubes for preparing clot (implant).

Still another aspect of the invention is to provide a novel formation of PRP/chitosan mixtures, which is prepared by mixing method 3 where the PRP/chitosan mixture was placed in glass tubes and then thrombin/$CaCl_2$ solution, was layered on top of the PRP/chitosan in the tube for preparing clot (implant).

The mixing method 3 was the best mixing method for the thrombin/$CaCl_2$ activator, resulting in the best clot properties, coagulating in a suitable time, no clot retraction, good mechanical properties and good homogeneity.

Still another aspect is to provide a novel formation of PRP/chitosan mixtures, which is prepared by syringe mixing method where the PRP/chitosan mixtures was mixed with the activator (thrombin/$CaCl_2$ solution: 1000 U/mL in 10% (w/w) $CaCl_2$ of initial) by using double syringe system, then transferred into glass tubes for preparing clot (implant).

Still another aspect is to provide a novel formation of thrombin free PRP/chitosan mixtures, which is prepared by just using $CaCl_2$ solution with different concentration (from 1.0% w/w to 25% w/w) as activator and mixing method 3 where the PRP/chitosan mixture was placed in glass tubes and then just $CaCl_2$ solution was layered on top of the PRP/chitosan for preparing clot (implant).

Still another aspect of the invention is to provide a novel formulation of thrombin free PRP/chitosan mixtures, which is prepared by just using $CaCl_2$ solution with different concentration (from 1.0% w/w to 25% w/w) as activator, where $CaCl_2$ was mixed into PRP/chitosan by 5 times gentle inversion of the mixing tube containing stainless steel beads and then drawn into a syringe for placement in glass tubes for preparing clot (implant).

Still another aspect is to provide a novel formation of thrombin free PRP/chitosan mixtures, which is prepared by just using $CaCl_2$ solution with lower concentration (1.0% w/w to 5% w/w) as activator, and using chitosan solution with different concentrations (1.0% w/w to 10.0% w/w) mixed with PRP at different mix ratios (PRP:chitosan is from 4:1 to 1:1 at volume ratio).

It is thus disclosed herein a novel formulation and/or method of preparing PRP/chitosan mixtures with thrombin, where the PRP/chitosan mixture was placed in glass tubes and then thrombin/$CaCl_2$ solution was layered on top of the PRP/chitosan in the tube for preparing implant (shown in Example 1 from human blood). Platelet rich plasma (PRP) was isolated from freshly drawn citrate anticoagulated whole blood with two-step centrifugation (1300 rpm for 10 minutes and then 2000 rpm for 10 minutes). Chitosan (1.62% w/w)-HCl (38 mM)-NaCl (160 mM) solution at pH of 6.54 and osmolality of 361 mOsm/kg, and chitosan (1.62% w/w)-HCl (71 mM)-βGP (2.15% w/w) solution at pH of 6.65 and osmolality of 342 mOsm/kg were mixed with PRP. 900 µl of platelet-rich plasma (PRP) was pipetted into cryotubes containing 300 µl of a chitosan solution and three 0.39 g stainless steel balls, mixed by hand for 10 seconds (shaken and reversed about 50 times vigorously). The mix ratio of PRP to chitosan was 3:1 at volume ratio.

300 µl was transferred into 3 glass tubes at 37° C. by using 1 ml syringe. Immediately 30 µl thrombin solution (1000 U/ml) diluted with sterile 10% (w/w) calcium chloride solution (mix ratio of PRP/chitosan to thrombin/$CaCl_2$ is 10 to 1) was added on the surface of PRP/chitosan mixture of each glass tube for preparing 3 clots (implants). Coagulation time test results showed PRP/chitosan-HCl—NaCl mixtures coagulated within 6 minutes and PRP/chitosan-HCl-βGP mixture formed clot within 8 minutes in the glass tube (see Table 2, FIGS. 1 and 2). For both of them, almost no liquid was expressed and the clot didn't retract.

Figure 3:
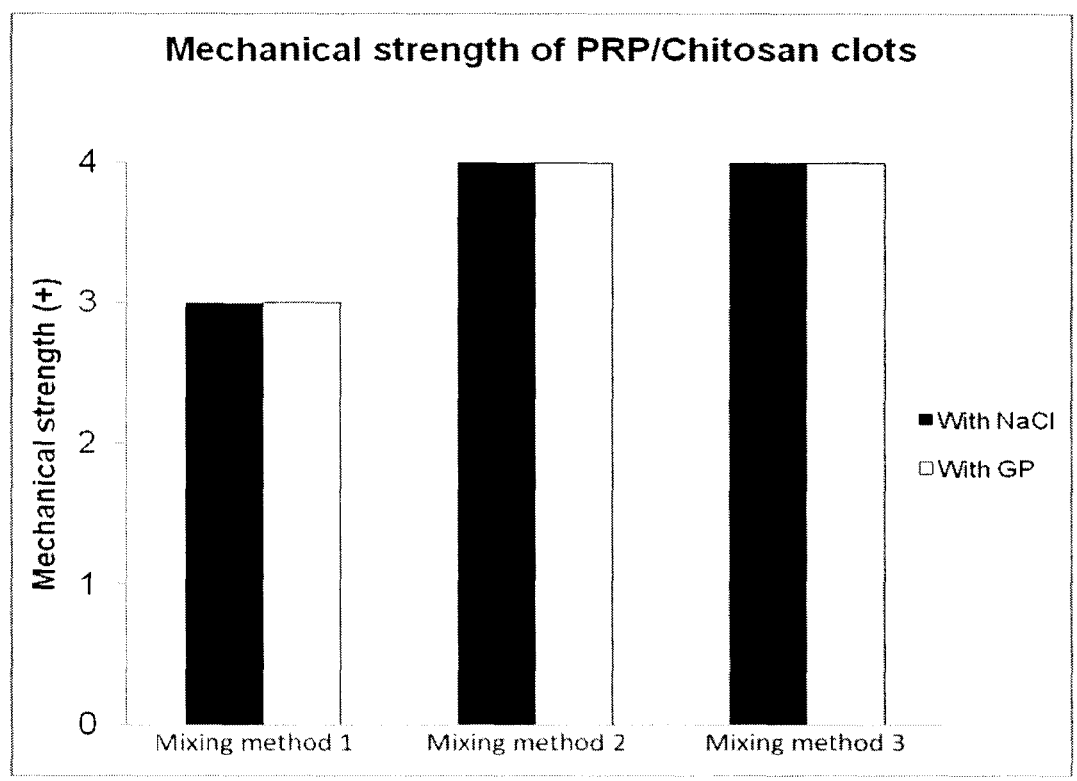
FIG. 3 is a histogram reflecting the mechanical strength of PRP/chitosan clots (PRP/chitosan-HCl—NaCl pH 6.6 or PRP/chitosan-HCl-βGP pH 6.6) prepared with thrombin/CaCl$_2$ activator by different mixing methods. Mixing method 1 was gentle inversion, mixing method 2 was drawing into a syringe without inversion and mixing method 3 was layering.
Figure 4:
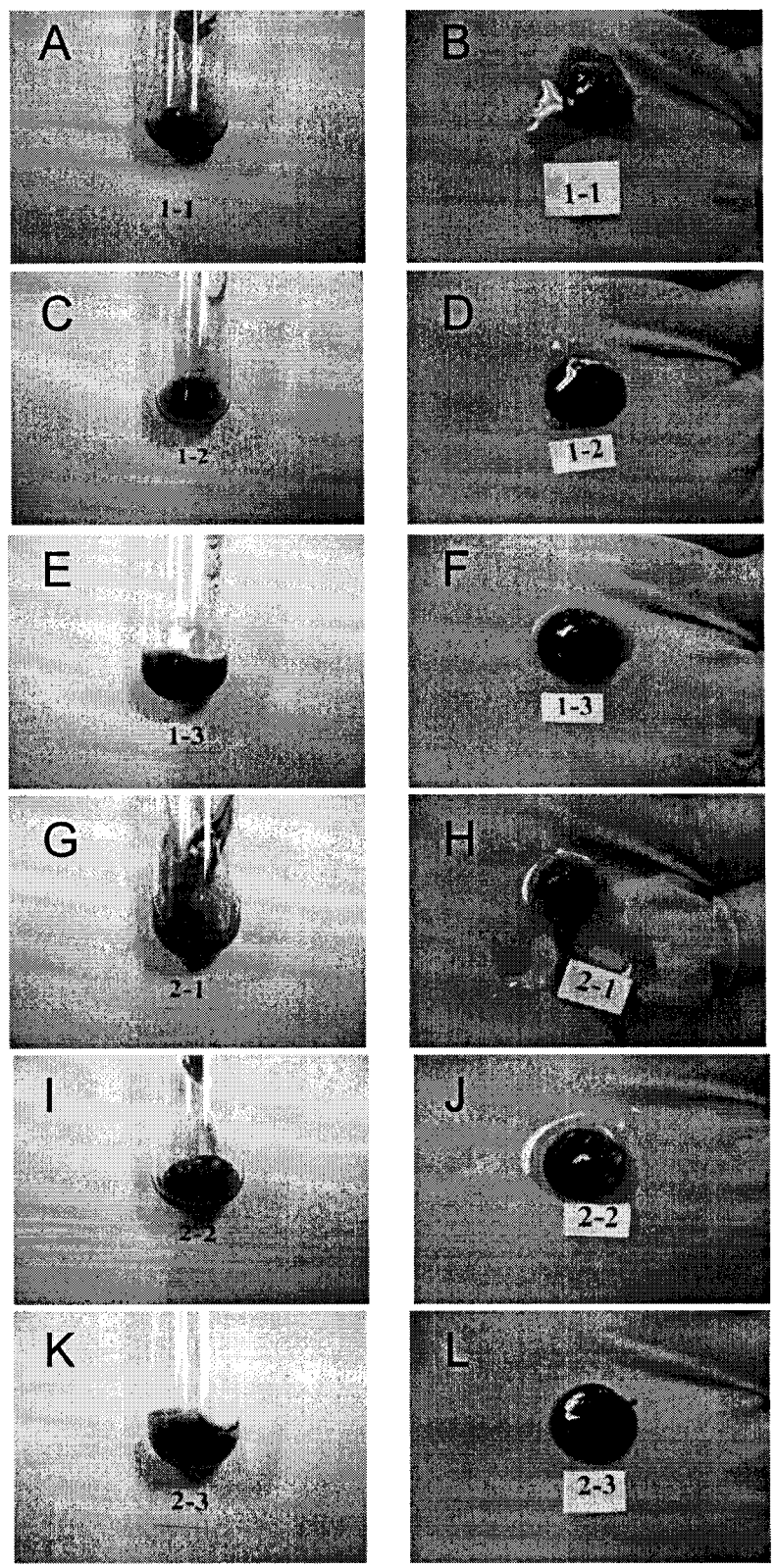
FIG. 4 corresponds to photographic representations of PRP/chitosan clots in the glass tubes (A, C, E, G, I, K) and after removal from the tubes (B, D, F, H, J, L) wherein the sample numbers are: 1-1 (with NaCl, mixing method 1); 1-2 (with NaCl, mixing method 2); 1-3 (with NaCl, mixing method 3); 2-1 (with βGP, mixing method 1); 2-2 (with βGP, mixing method 2); 2-3 (with βGP, mixing method 3).

The PRP/chitosan clots made by this mixing method/activator combination were firm and elastic, the mechanical strength of the clots were ++++ (Table 3, FIGS. 3 and 4). The homogeneity of the clots (Table 4) was better than the homogeneity of clots made by mixing method 2 (1 sample was "±", 1 was "−") and better than the homogeneity of clots made by mixing method 1 (both were "−"). Mixing method 3 resulted in the best clot properties, coagulated in a suitable time, with no clot retraction, good mechanical properties and good homogeneity. Similar results were also obtained from rabbit blood.

The current description also provides a novel formation of thrombin free PRP/chitosan mixtures (shown in Example 3), prepared by just using $CaCl_2$ solution with lower concentration (1.3% w/w and 3% w/w) as activator, and using chitosan solution with different concentrations (1.62% w/w and 2% w/w) mixed with PRP at different mix ratios (PRP:chitosan ratio is 3:1 or 2:1). Platelet rich plasma (PRP) was isolated from freshly drawn citrate anticoagulated whole blood with two-step centrifugation (1300 rpm for 10 minutes and then 2000 rpm for 10 minutes). Chitosan (1.62% w/w)-HCl (38 mM)-NaCl (160 mM) solution at pH of 6.56 and osmolality of 344 mOsm/kg, and chitosan (2.0% w/w)-HCl (50 mM)-NaCl (150 mM) solution at pH of 6.49 and osmolality of 324 mOsm/kg were used to mix with PRP. To prepare the PRP/chitosan mixture at mix ratio of 3:1 (v/v), 0.9 mL of platelet-rich plasma (PRP) was pipetted into the cryotubes containing 300 µL 1.62% w/w chitosan (or 2.0% w/w chitosan) solution and three 0.39 g stainless steel balls, mixed by hand for 10 seconds (shaken and reversed about 50 times vigorously). 300 µL was transferred into 3 glass tubes at 37° C. by using 1 ml syringe. Immediately 60 µl 1.3% (w/w) calcium chloride solution (or 3% w/w $CaCl_2$ solution) was instilled very carefully and slowly on the surface of PRP/chitosan mixture of each glass tube for preparing 3 clots (the mix ratio of PRP/chitosan to $CaCl_2$ solution was 5 to 1 at volume ratio).

Figure 9:
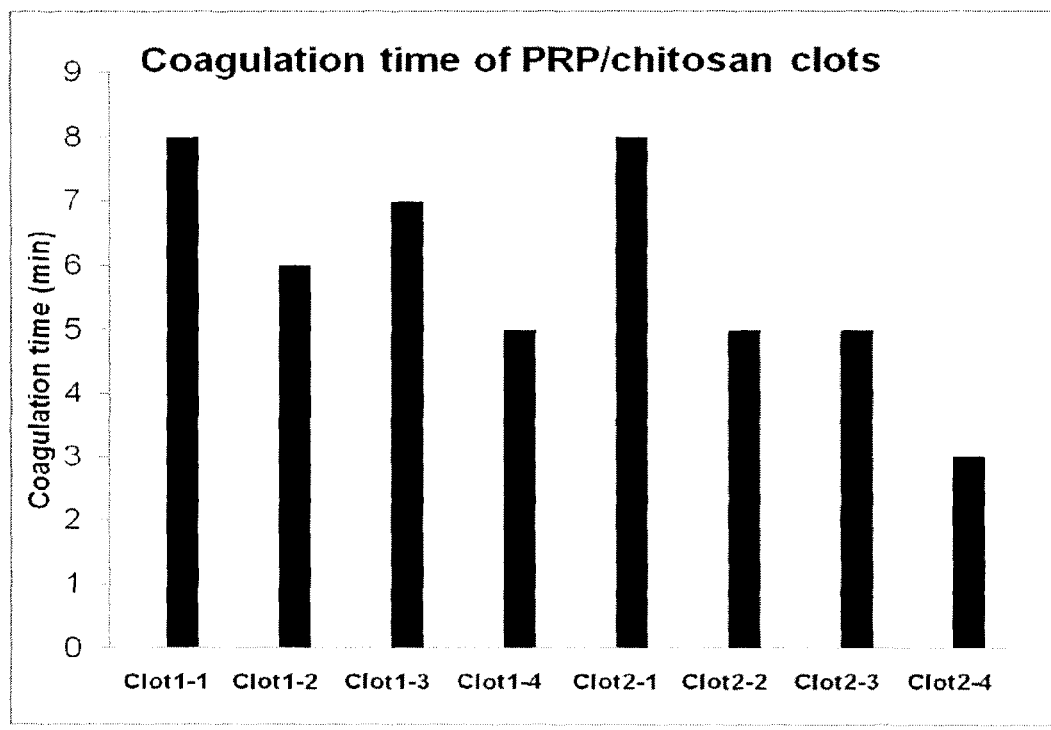
FIG. 9 is a histogram reflecting the coagulation time of PRP/chitosan-HCl—NaCl pH 6.6 mixtures with different chitosan and CaCl$_2$ concentrations and at different mix ratios wherein the sample numbers are: 1-1 (1.3% CaCl$_2$, mix ratio 3:1, 1.62% chitosan); 1-2 (1.3% CaCl$_2$, mix ratio 3:1, 2% chitosan); 1-3 (1.3% CaCl$_2$, mix ratio 2:1, 1.62% chitosan); 1-4 (1.3% CaCl$_2$, mix ratio 2:1, 2% chitosan); 2-1 (3% CaCl$_2$, mix ratio 3:1, 1.62% chitosan); 2-2 (3% CaCl$_2$, mix ratio 3:1, 2% chitosan); 2-3 (3% CaCl$_2$, mix ratio 2:1, 1.62% chitosan); 2-4 (3% CaCl$_2$, mix ratio 2:1, 2% chitosan).
Figure 10:
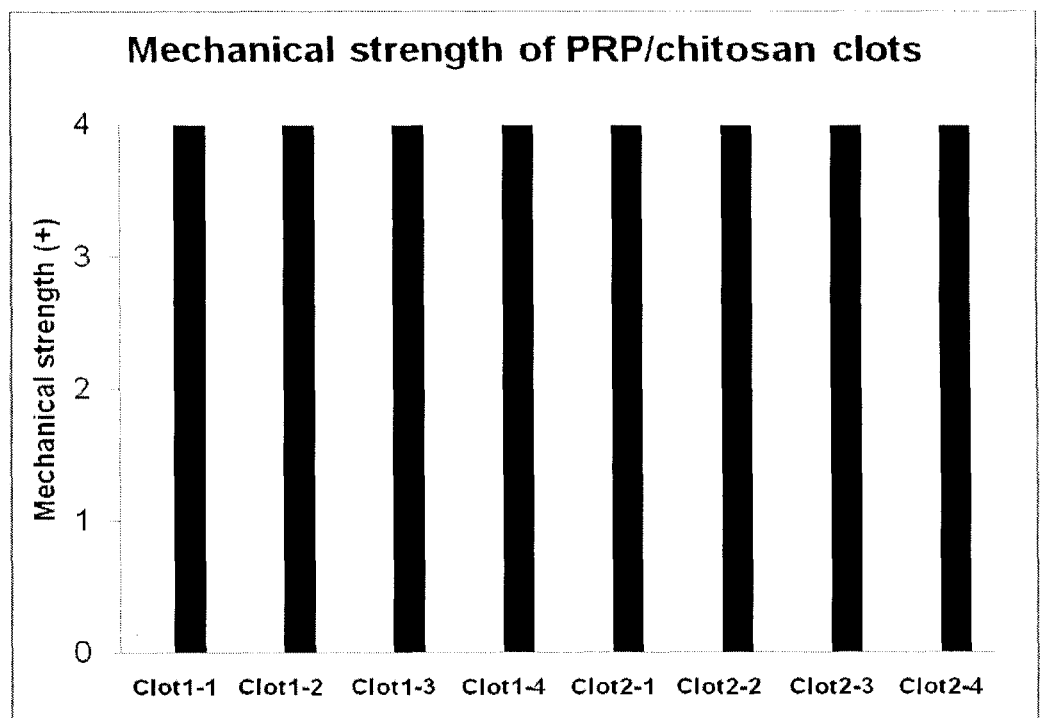
FIG. 10 is a histogram reflecting the mechanical strength of PRP/chitosan-HCl—NaCl pH 6.6 clots with different chitosan and CaCl$_2$ concentrations and at different mix ratios wherein the sample numbers are: 1-1 (1.3% CaCl$_2$, mix ratio 3:1, 1.62% chitosan); 1-2 (1.3% CaCl$_2$, mix ratio 3:1, 2% chitosan); 1-3 (1.3% CaCl$_2$, mix ratio 2:1, 1.62% chitosan); 1-4 (1.3% CaCl$_2$, mix ratio 2:1, 2% chitosan); 2-1 (3% CaCl$_2$, mix ratio 3:1, 1.62% chitosan); 2-2 (3% CaCl$_2$, mix ratio 3:1, 2% chitosan); 2-3 (3% CaCl$_2$, mix ratio 2:1, 1.62% chitosan); 2-4 (3% CaCl$_2$, mix ratio 2:1, 2% chitosan).

To prepare the PRP/chitosan mixture at mix ratio of 2:1 (v/v), all the procedures described above were repeated by pipetting 0.8 mL of PRP into 400 µl chitosan solution. Coagulation time test results (Table 10 and FIG. 9) showed that all the mixtures coagulated within 8 minutes. For the same mix ratio, more concentrated chitosan solutions needed less time to clot (2.0% vs 1.62%). For the same chitosan concentration, PRP mixed with more chitosan solution needed less time to clot (mix ratio of 2:1<mix ratio of 3:1). At the same chitosan concentration and mix ratio, the mixtures activated with 3% $CaCl_2$ solution coagulated slightly faster than the mixtures activated with 1.3% $CaCl_2$ solution (coagulation time was shorter for 3 of 4 samples). Mechanical strength results showed (see Table 11, FIG. 10) that all eight clots didn't retract significantly, but the clots prepared with 2% chitosan appeared to express less liquid than the clots prepared with 1.62% chitosan. Although the mechanical strength scores were identical for all samples, the mechanical strength of the clots prepared with 2% chitosan appeared slightly better (after crushing, 2 of 4 samples showed just a hole in the center of clots, 1 of 4 samples was broken into two connected fragments and 1 of 4 samples was broken into two fragments) than the clots prepared with 1.62% chitosan (after crushing, 4 of 4 samples were broken into two connected fragments).

The homogeneity evaluation results (Table 12) demonstrated that the homogeneity of all eight clots was satisfactory (all of them were above ±). The homogeneity of clots prepared with 1.3% $CaCl_2$ solution (3 of 4 samples were +, 1 of 4 was between ± and +) was better than the homogeneity of the clots prepared with 3% $CaCl_2$ solution (1 of 4 sample was +, 3 of 4 samples were between ± and +).

In summary, PRP/chitosan-HCl—NaCl clots with good properties can be prepared by mixing PRP with 2.0% or 1.62% w/w chitosan solutions at both mix ratios of 2:1 or 3:1 v/v, and activating with 1.3% or 3% w/w $CaCl_2$ solutions. The PRP/chitosan-HCl—NaCl mixtures prepared with 2.0% chitosan solution at mix ratio of 2:1 (v/v), using 3% w/w $CaCl_2$ solution as activator, resulted in the best clot properties, clotting in a suitable time, with no clot retraction, good mechanical properties and good homogeneity. The use of a higher concentration (2%) and greater mix ratio of chitosan solution to PRP resulted in more attractive handling properties since these mixtures were more paste-like and more viscous and thus easier to apply in cartilage defects and to other sites that are challenging for delivery.

The current invention also provides another novel formation of thrombin free PRP/chitosan mixtures (shown in Example 4), prepared by adding 3% w/w $CaCl_2$ solution to PRP/chitosan mixture and mixing it gently by inverting the tube 5 times in 5 seconds, and then transferring in glass tubes with a syringe to prepare the clot (implant). Platelet rich plasma (PRP) was isolated from freshly drawn citrate anticoagulated whole blood with two-step centrifugation (1300 rpm for 10 minutes and then 2000 rpm for 10 minutes). PRP was mixed with chitosan solution with different molecular weight (CH0100702B—$M_n$ 232 kDa, 81% DDA and CH0050602A—$M_n$ 298 kDa, 76% DDA) and similar physiological pH and osmolality at mix ratio of 3:1. To prepare the PRP/chitosan mixture: 0.9 mL of platelet-rich plasma (PRP) was pipetted into the cryotubes containing 300 μL 1.62% w/w chitosan solution and three 0.39 g stainless steel balls, mixed by hand for 10 seconds (shaken and reversed about 50 times vigorously). 240 μL 3% w/w $CaCl_2$ solution was added to PRP/chitosan mixture and mixed gently by inverting the tube 5 times in 5 seconds. About 300 μL of mixture was then transferred into three glass tubes for preparing 3 clots.

Figure 11:
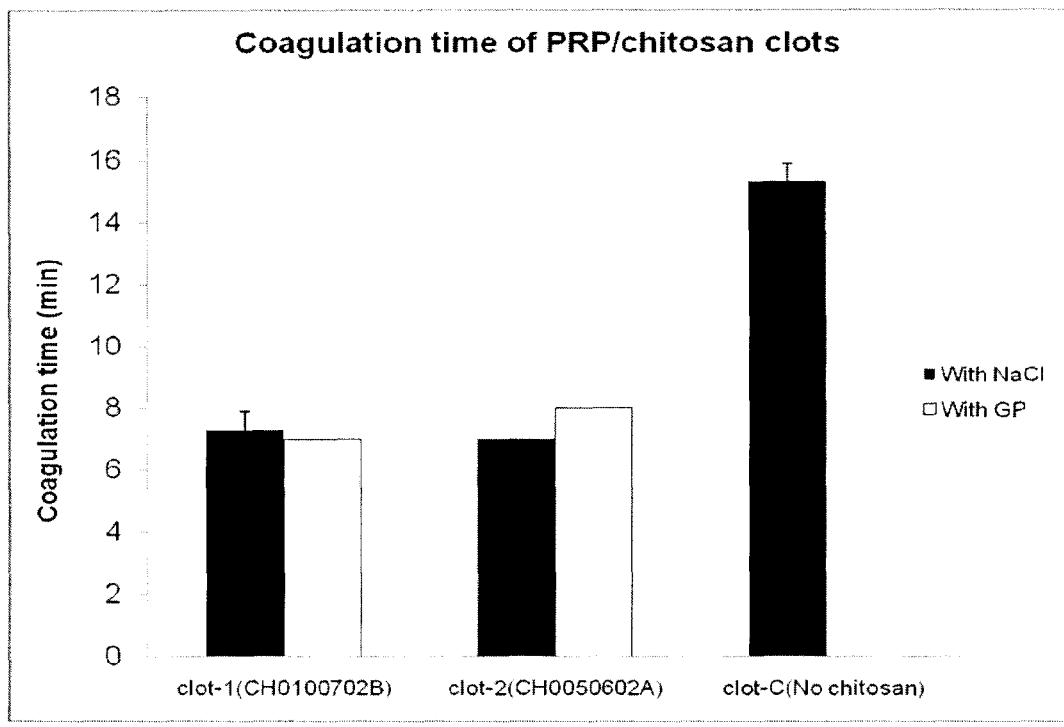
FIG. 11 is a histogram reflecting coagulation time of PRP/chitosan-HCl—NaCl pH 6.6 or PRP/chitosan-HCl-βGP pH 6.6 clots activated by gentle inversion with CaCl$_2$ (all clots are at 1.62% chitosan, mix ratio 3:1) wherein the sample numbers are: clot-1 (CH0100702B: $M_n$ 232 kDa, 81% DDA); clot-2 (CH0050602A: $M_n$ 298 kDa, 76% DDA); control (pure PRP).

Results showed that all the mixtures prepared with chitosan CH0100702B ($M_n$ 232 kDa, 81% DDA) coagulated within 8 minutes. The coagulation time of PRP/chitosan-HCl—NaCl clots was near equal to the coagulation time of PRP/chitosan-HCl-βGP clots (average was 7.3 minutes versus 7 minutes respectively) (Table 15 and FIG. 11). All the mixtures prepared with chitosan CH0050602A ($M_n$ 298 kDa, 76% DDA) coagulated within 8 minutes. The coagulation time of PRP/chitosan-HCl—NaCl clots was near equal to the coagulation time of PRP/chitosan-HCl-βGP clots (average was 7 minutes versus 8 minutes respectively) (Table 16 and FIG. 11).

Figure 12:
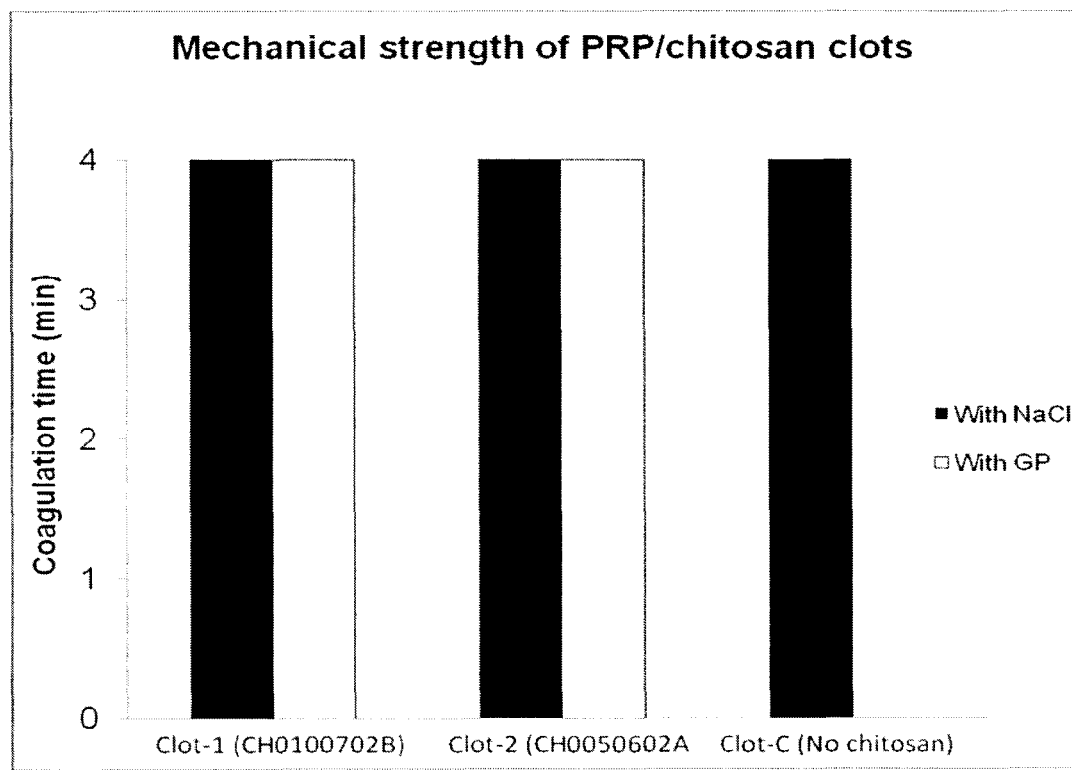
FIG. 12 is a histogram reflecting the mechanical strength of PRP/chitosan-HCl—NaCl pH 6.6 or PRP/chitosan-HCl-βGP pH 6.6 clots activated by gentle inversion with CaCl$_2$ (all clots are at 1.62% chitosan, mix ratio 3:1) wherein the sample numbers are: clot-1 (CH0100702B: $M_n$ 232 kDa, 81% DDA); clot-2 (CH0050602A: $M_n$ 298 kDa, 76% DDA); control (pure PRP).
Figure 13:
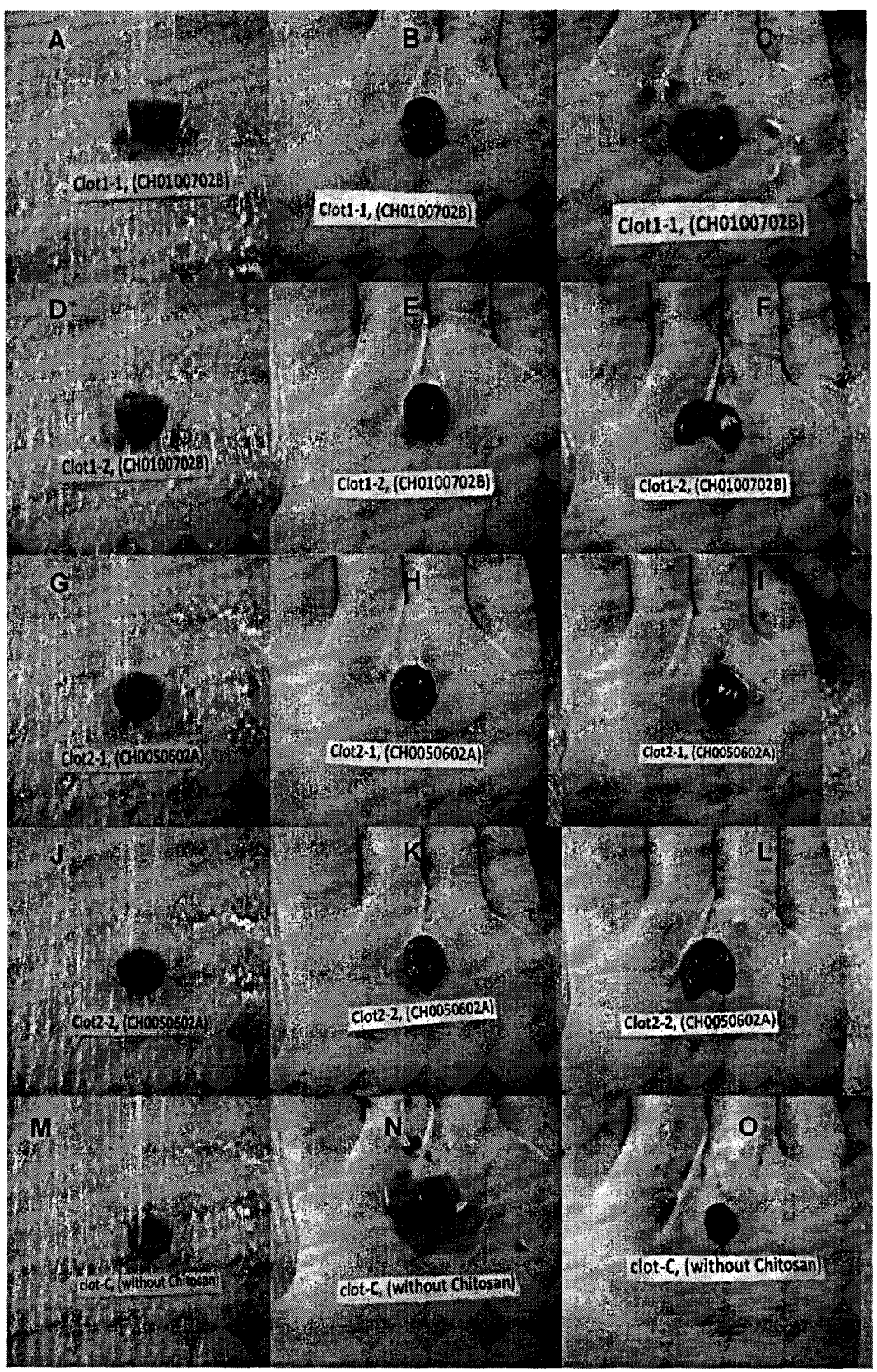
FIG. 13 corresponds to photographic representations of PRP/chitosan clots activated by gentle inversion with CaCl$_2$ (all clots are at 1.62% chitosan, mix ratio 3:1) in the glass tubes (A, D, G, J, M), after removal from the tubes (B, E, H, K, N) and after mechanical strength test (C, F, I, L, O) wherein the sample numbers are: 1-1 (with NaCl; $M_n$ 232 kDa, 81% DDA); 1-2 (with βGP; $M_n$ 232 kDa, 81% DDA); 2-1 (with NaCl; $M_n$ 298 kDa, 76% DDA); 2-2 (with βGP; $M_n$ 298 kDa, 76% DDA); control (pure PRP).
Figure 14:
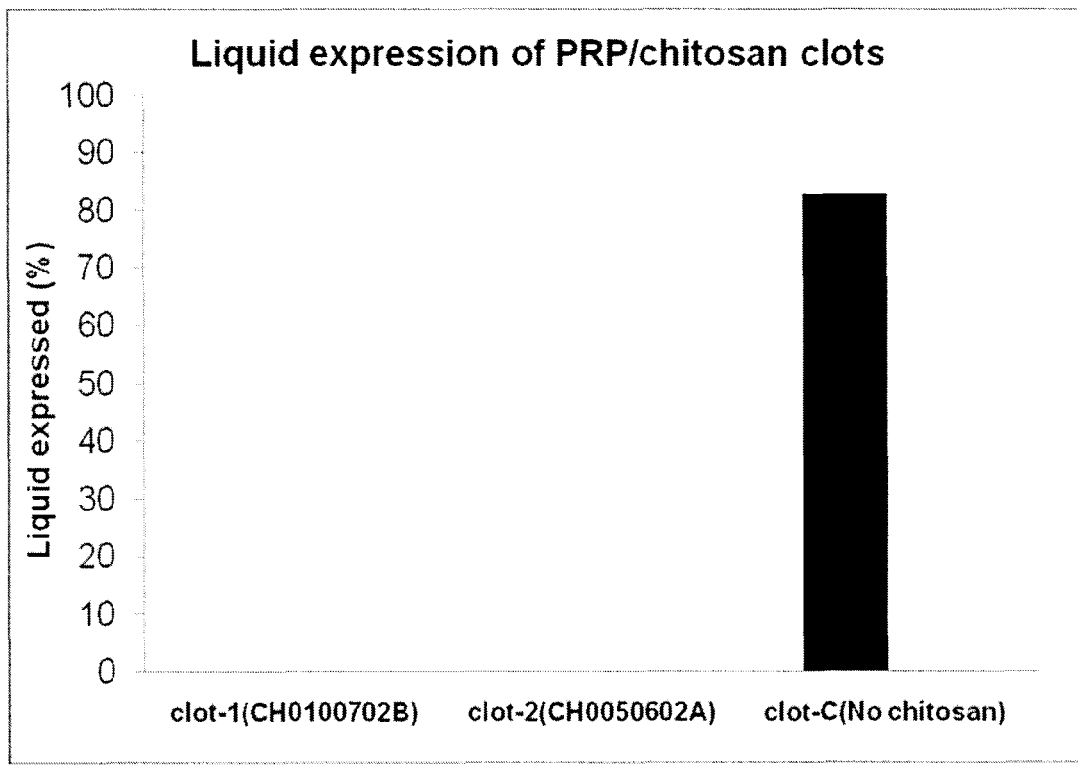
FIG. 14 is a histogram reflecting liquid expressed by PRP/chitosan clots activated by gentle inversion with CaCl$_2$ (all clots are at 1.62% chitosan, mix ratio 3:1) wherein the sample numbers are: Clot-1 (CH0100702B: $M_n$ 232 kDa, 81% DDA); Clot-2 (CH0050602A: $M_n$ 298 kDa, 76% DDA); control (pure PRP).

The mechanical strength test results showed that all the clots prepared by gentle inversion following $CaCl_2$ activation were firm and elastic, the mechanical strength of all the clots was "++++". There was no significant difference in mechanical strength between PRP/chitosan-HCl—NaCl clots and PRP/chitosan-HCl-βGP clots. There was no significant difference in mechanical strength among the clots prepared with the different chitosans as well (Table 17 and FIG. 12). After 60 minutes, none of the clots expressed any liquid and retracted, the clots were perfectly intact. Meanwhile, the PRP clot without chitosan expressed a lot of liquid (82.9%) and retracted significantly (Table 17, FIG. 13 and FIG. 14).

In conclusion, gentle inversion of the cryotube after adding the $CaCl_2$ activator does not seem to interrupt the coagulation process and affect coagulation time. The PRP/chitosan clots prepared by the gentle inversion mixing method express no liquid, do not retract, have good mechanical strength and clot in suitable time. The gentle inversion method is easier to translate to clinical application.

The compositions described herein can be used to improve the repair and to regenerate cartilaginous tissues and other tissues including without limitation meniscus, ligament, tendon, bone, skin, cornea, periodontal tissues, abscesses, resected tumors, and ulcers.

There is also contemplated herein the use of the polymer compositions described herein that can be placed or injected into a body site where the mixture aids the repair, regeneration, reconstruction or bulking of tissues. Repaired tissues include for example without limitation cartilage, meniscus, ligament, tendon, bone, skin, cornea, periodontal tissues, abscesses, resected tumors, and ulcers. The tissue that can be repaired or regenerated is for example without limitation cartilage, meniscus, ligament, tendon, bone, skin, cornea, periodontal tissue, abscesses, resected tumors, or ulcers. In some cases, the site of introduction in the body may be surgically prepared to remove abnormal tissues. Such procedure can be done by piercing, abrading or drilling into adjacent tissue regions or vascularized regions to create channels for the polymer composition to migrate into the site requiring repair.

The present disclosure will be more readily understood by referring to the following examples which are given to illustrate embodiments rather than to limit its scope.

EXAMPLE 1

Formulation and Characterization of PRP/Chitosan Clots Activated by Thrombin and Prepared with Different Mixing Methods (Human Blood)

1—Preparation of Chitosan (1.62% w/w)-HCl (38 mM)-NaCl (160 mM) Solution; without NaOH, pH: 6.6; Total Volume: 10.0 ml 0.180 g of chitosan ($M_n$ 232 kDa, 81% DDA) was weighed in a 20 ml beaker, $H_2O$dd was added to the beaker, until the weight of chitosan+$H_2O$=9.34 g. A magnetic stir bar was inserted into the beaker; the solution stirred for about 10 minutes in order to hydrate the chitosan powder as much as possible. 0.38 ml of HCl 1 N (Sigma, Product No. 318949) was added to the solution under moderate stirring.

The beaker was covered with Parafilm™, and the solution heated to about 60° C. for 2 hours, stirred overnight until completely dissolved. 0.32 ml of 5N NaCl (Sigma, Product No S-9888) solution was added into the beaker and well mixed. The pH of the chitosan solution was physiological at 6.5 and the osmolality was also physiological 361 mOsm/kg (Table 1).

2—Preparation of Chitosan (1.62% w/w)-HCl (71 mM)-βGP (2.15% w/w) Solution, pH: 6.6, total volume: 9.0 ml 0.162 g of chitosan ($M_n$ 232 kDa, 81% DDA) was weighed in a 20 ml beaker, $H_2O$ dd added to the beaker, until the weight of chitosan+$H_2O$=6.65 g. A magnetic stir bar was added into the beaker; the solution stirred for about 10 minutes in order to hydrate the chitosan powder as much as possible. 0.55 ml of HCl 1 N (Sigma, Product No 318949) was added to the solution under moderate stirring. The beaker was covered with Parafilm™ and stirred overnight until completely dissolved. 1.8 ml of 10.75% w/w βGP (Sigma, Product No G9891) in 50 mM HCl was added into the beaker and well mixed (mix ratio of chitosan solution/βGP solution is 4:1). The pH of the chitosan solution was physiological at 6.7 and the osmolality was also physiological, at 342 mOsm/kg (Table 1).

TABLE 1

Composition and properties of chitosan solutions.

| Solution | $C_{chitosan}$ (% w/w) | $C_{HCl}$ (mM) | $C_{NaCl}$ (mM) | $C_{\beta GP}$ (% w/w) | Precipitation | pH (Measured) | Osmolality (mOsm/kg) |
|---|---|---|---|---|---|---|---|
| 1. Chitosan-HCl—NaCl pH 6.6 | 1.62 | 38 | 160 | no | no | 6.54 | 361 |
| 2. Chitosan-HCl-βGP pH 6.6 | 1.62 | 71 | no | 2.15 | no | 6.65 | 342 |

3—Drawing Blood

About 40 cc whole blood was extracted from a donor with informed consent using blood-taking IRB protocol. First, ~2 ml of blood was collected in a Vacutainer® tube containing EDTA (Fisher, BD, Product No 02-683-99A) to obtain CBC (complete blood count) and platelet counts. Second, ~35 ml of blood was collected in 4 Vacutainer® tubes containing ACD (VWR, BD, Product No VT4606) to prepare platelet-rich plasma (PRP). Each Vacutainer® tube can contain up to 8.5 ml blood.

4—Isolating PRP from Anti-Coagulated Whole Blood

The ACD-Vacutainer® tubes containing whole blood were centrifuged in the ACE E-Z PRP™ centrifuge at 1300 rpm for 10 minutes at room temperature in order to separate the erythrocytes from the plasma and buffy coat containing leukocytes and platelets. The supernatant fractions containing plasma and the buffy coat were removed using a 2½ inch (18 gauge) blunt needle (ACE, Product No 09-002-69) attached to a 10 ml syringe (Fisher, BD, Product No 309604). The straw colored liquid was drawn into the syringe until the needle reached into the first 1-2 mm of the layer of red blood cells. The first 1-2 mm of erythrocytes was taken to ensure that the entire buffy coat (i.e., white blood cell fraction) was collected. The plasma and buffy coat fractions were expressed from the syringe into new Vacutainer® tubes (washed and depyrogenized) containing no anti-coagulant. The plasma and buffy coat were further centrifuged at 2000 rpm for 10 minutes at room temperature in order to separate platelet-rich plasma (PRP) from platelet poor plasma (PPP). The Vacutainer® tubes were transferred to a Vacutainer® holder and the caps removed. The yellow supernatant (PPP) fractions were removed using the same 2½ inch blunt needle (18 gauge) and a new 10 ml syringe. A small volume of yellow supernatant (PPP) was left in the Vacutainer® tubes, leaving approximately 1.5 ml of PRP containing some PPP in the bottom fraction of the Vacutainer® tubes. The top PPP fractions were expressed from the syringe into a sterile Falcon tube. The 1.5 ml of PRP in the bottom fraction of the Vacutainer® tubes was gently mixed by drawing and expressing the liquid 3 times using the 3 inch blunt needle (18 gauge, ACE, Product No 09-002-70) attached to a 10 ml syringe. The PRP fraction was stored at room temperature until further use. About 6.0 ml PRP was harvested from about 35 ml ACD blood collected from the donor.

5—Preparing the Thrombin Coagulation Solutions

To prepare the 10% (w/w) calcium chloride solution, 1.99 g of $CaCl_2.2H_2O$ (Sigma, Product No C7902-500G) was weighed in a 50 ml beaker, $H_2O$dd added to the beaker, until the weight of $CaCl_2.2H_2O+H_2O$=15 g. A magnetic stir bar was inserted into the beaker, and the solution was stirred until completely dissolved. The thrombin solution (1000 U/ml) was prepared by diluting the thrombin powder with the 10% (w/w) calcium chloride solution. For this particular experiment, an entire vial (1000 U, Sigma, Product No T7009-1KU) of thrombin was diluted with 1.0 ml of 10% (w/w) calcium chloride solution. The thrombin solution was stored on ice until use.

6—Preparing Chitosan/PRP Clots and Measuring the Coagulation Time and Mechanical Strength of the Clots To prepare the chitosan-HCl—NaCl (pH 6.6)/PRP clots coagulated with thrombin/calcium chloride (1000 U/ml), 900 μl of platelet-rich plasma (PRP) was pipetted into cryotubes containing 300 μl chitosan solution and three 0.39 g stainless steel balls, mixed by hand for 10 seconds (shaken and reversed about 50 times vigorously). One of the following 3 mixing procedure was then used.

Mixing method #1—inversed 5 times then drawn into syringe: 133 μl thrombin solution (1000 U/ml) diluted with sterile 10% (w/w) calcium chloride solution was immediately added to the PRP/chitosan mixture and mixed well by inversion for 5 seconds (inverting the tube 5 times gently). To prepare the clots, 300 μl were transferred into 3 glass tubes at 37° C. with a 1 ml syringe. Three clots were prepared: 1 clot was used to test coagulation time and fixed immediately after it coagulated, 1 clot was used to test coagulation time and fixed after 60 minutes, and 1 clot was used to test coagulation time and mechanical strength.

Mixing method #2—no inversion, just drawn into syringe: 133 μl thrombin solution (1000 U/ml) diluted with sterile 10% (w/w) calcium chloride solution was added on the surface of PRP/chitosan mixture. The mixture was immediately drawn into a 1 ml syringe and 300 μl transferred into 3 glass tubes at 37° C. Three clots were prepared: 1 clot was used to test coagulation time and fixed immediately after it coagulated, 1 clot was used to test coagulation time and fixed after 60 minutes, and 1 clot was used to test coagulation time and mechanical strength.

Mixing method #3—layered on top: 300 µl of PRP/chitosan mixture was transferred into 3 glass tubes at 37° C. with a 1 ml syringe. 33 µl thrombin solution (1000 U/ml) diluted with sterile 10% (w/w) calcium chloride solution was immediately added on the surface of PRP/chitosan mixture of each glass tube to prepare 3 clots: 1 clot was used to test coagulation time and fixed immediately after it coagulated, 1 clot was used to test coagulation time and fixed after 60 minutes, and 1 clot was used to test coagulation time and mechanical strength.

To prepare the PRP/chitosan-HCl-βGP (pH 6.6) clots coagulated with thrombin/calcium chloride (1000 U/ml), 900 µl of platelet-rich plasma (PRP) was pipetted into cryotubes containing 300 µl chitosan solution and three 0.39 g stainless steel balls, mixed by hand for 10 seconds (shaked and reversed about 50 times violently). Then the above 3 mixing procedures were repeated.

Coagulation was determined by visualization of the clot at 37° C. The glass tubes were taken from the hot plate vertically every minute, the tube slowly tilted, the blood mixture visualized on the bottom of tube. If the mixture was immobile and formed a clot, then it was coagulated; if the mixture was still mobile at the bottom of the tube, it had not coagulated yet. Mechanical strength was tested by putting the clot on the centre of the palm, the clot pressed with a finger until crushed; the resistance observed to compression, liquid expression and crushed appearance were monitored. The mechanical strength was scored with the 4 "+" system: "+" represents clot was easily broken and crushed appearance was multiple fragments (more than 5 fragments); "++" represents clot was relatively firm and crushed appearance was multiple fragments (3-5 fragments); "+++" represents clot was firm and elastic, crushed appearance was 2-3 fragments; "++++" represents clot was firm and elastic, crushed appearance was 2 fragments (sometimes still connected) or there was just a hole in the center of the clot.

Coagulation time (Table 2, FIGS. 1 and 2) results showed that all PRP/chitosan mixtures coagulated within 10 minutes (from a couple of seconds to 10 minutes). For mixing method 1 where thrombin was mixed into PRP/chitosan by 5 times gentle inversion of the mixing tube containing stainless steel beads and then taken into a syringe for placement in glass tubes: coagulation occurred when the mixture was transferred by syringe and it was difficult to transfer the PRP/chitosan mixture into glass tubes (Table 2, FIGS. 1 and 2). A lot of liquid was expressed (++++, clots started to express liquid at 4 minutes after coagulation). The clots retracted significantly resulting in a shrunken clot immersed in serum. The PRP/chitosan clots made by this method were firm and elastic, the mechanical strength was +++(Table 3, FIGS. 3 and 4). These results suggest that bead mixing after thrombin/$CaCl_2$ activation results in clot retraction and a relative weak clot compared to the other two mixing methods.

Figure 2:
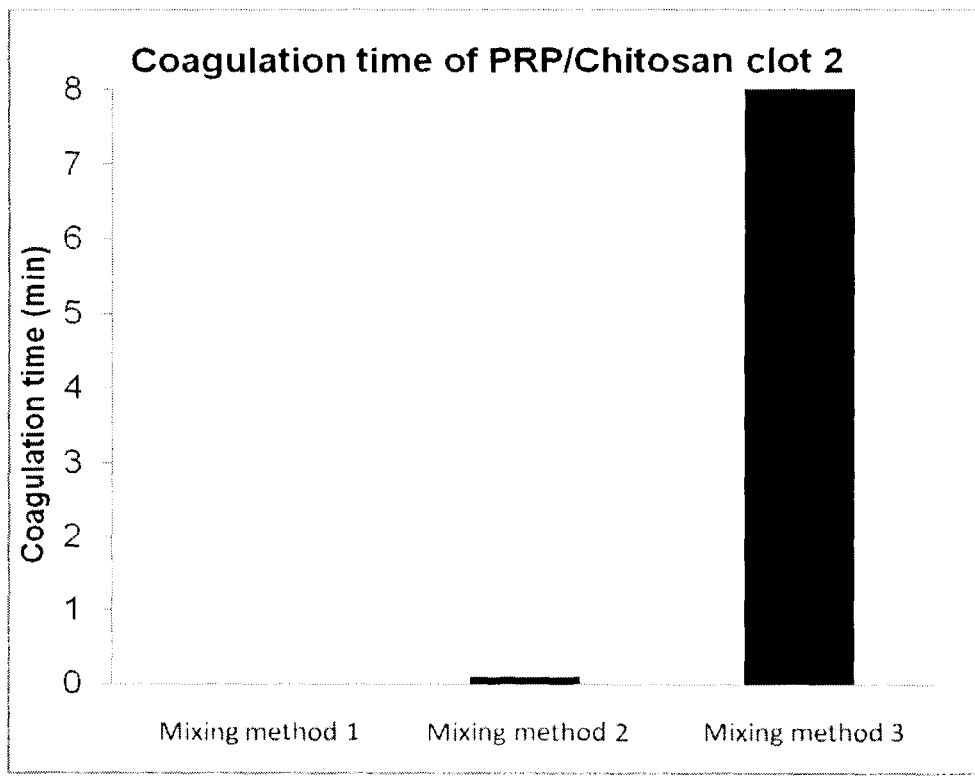
FIG. 2 is a histogram reflecting the coagulation time of PRP/chitosan clots-2 (PRP/chitosan-HCl-βGP pH 6.6) prepared with thrombin/$CaCl_2$ activator by different mixing methods. Mixing method 1 was gentle inversion, mixing method 2 was drawing into a syringe without inversion and mixing method 3 was layering.

For mixing method 2 where thrombin was added to the PRP/chitosan without inversion and directly drawn into the syringe for placement in glass tubes, coagulation occurred immediately after placement in glass tubes (less than 10 seconds; see Table 2, FIGS. 1 and 2). Some liquid was expressed (++, clots started to express liquid at 30 minutes for clot 1 and at 35 minutes for clot 2 after preparing clots). The clots retracted significantly. The PRP/chitosan clots made by this method were firm and elastic, the mechanical strength was ++++ (Table 3, FIGS. 3 and 4). These result suggest that clots made by this mixing method have improved mechanical properties (++++) but still retract.

For mixing method 3 where the PRP/chitosan mixture was placed in glass tubes and then thrombin was layered on top of the PRP chitosan in the tube, coagulation occurred at 6-8 minutes in the glass tube. PRP/chitosan-HCl—NaCl mixture coagulated after 6 minutes and PRP/chitosan-HCl-βGP mixture formed clot after 8 minutes in the glass tube (Table 2, FIGS. 1 and 2). Almost no liquid was expressed and the clots didn't retract. The PRP/chitosan clots made by this mixing method were firm and elastic, the mechanical strength was ++++ (Table 3, FIGS. 3 and 4). These results confirm that mixing method 3 results in the best clot properties, with no retraction following activation by thrombin/$CaCl_2$.

TABLE 2

Coagulation time of PRP/chitosan mixtures.

| Mixture | Sample number | Coagulation time (Min) | Mean value (Min) | Comments |
|---|---|---|---|---|
| PRP/chitosan-HCl—NaCl pH 6.6 (clot1) | Mixing method 1 (After adding thrombin, invert the cryotube 5 times in 5 seconds, then transfer into glass tubes) | 1<br>2<br>3 | —<br>—<br>— | — | All the samples coagulate within 10 minutes. Transfer into glass tubes was difficult following mixing method 1 since the mixture collated instantaneously; clots also coagulated too quickly with mixing method 2. The clot retracted a lot and expressed a lot of liquid (++++) after coagulation with mixing method 1; some liquid was expressed (++) and clots retracted a little with mixing method 2; the clots didn't retract and expressed little liquid (+) with mixing method 3. Results showed that mixing |
| | Mixing method 2 (Add thrombin solution on the surface of PRP/chitosan mixture, then directly transfer into glass tubes) | 1<br>2<br>3 | <10 Seconds<br><10 Seconds<br><10 Seconds | — | |
| | Mixing method 3 (Transfer PRP/chitosan mixture into glass tubes, then add thrombin solution on the mixture surface) | 1<br>2<br>3 | 6<br>6<br>6 | 6 | |

TABLE 2-continued

Coagulation time of PRP/chitosan mixtures.

| Mixture | Sample number | Coagulation time (Min) | Mean value (Min) | Comments |
|---|---|---|---|---|
| PRP/chitosan-HCl-βGP pH 6.6 (clot2) | Mixing method 1 (After adding thrombin, invert the cryotube 5 times in 5 seconds, then transfer into glass tubes) | 1<br>2<br>3 | —<br>—<br>— | —  | method 3 was the best choice to prepare PRP/chitosan clost following thrombin/CaCl$_2$ activation (Suitable coagulation time, good clot shape and good mechanical strength). |
| | Mixing method 2 (Add thrombin solution on the surface of PRP/chitosan mixture, then directly transfer into glass tubes) | 1<br>2<br>3 | <10 Seconds<br><10 Seconds<br><10 Seconds | — | |
| | Mixing method 3 (Transfer PRP/chitosan mixture into glass tubes, then add thrombin solution on the mixture surface) | 1<br>2<br>3 | 8<br>8<br>8 | 8 | |

"—" means the mixture coagulated during transfer and can be estimated as "0".

TABLE 3

Mechanical strength test of PRP/chitosan clots.

| Sample | Resistance to compression | Liquid expressed | Crushed appearance |
|---|---|---|---|
| Chitosan-HCl—NaCl(pH 6.6)/PRP clot1-1 (1000 U/ml) | Firm and elastic +++ | A lot of liquid expressed ++++ | 2-3 fragments) |
| Chitosan-HCl—NaCl(pH 6.6)/PRP clot1-2 (1000 U/ml) | Firm and elastic ++++ | Some liquid expressed ++ | Break into 2 fragments but still connected |
| Chitosan-HCl—NaCl (pH 6.6)/PRP clot1-3 (1000 U/ml) | Firm and elastic ++++ | Little liquid expressed + | Break into 2 fragments |
| Chitosan-HCl-βGP (pH 6.6)/PRP clot2-1 (1000 U/ml) | Firm and elastic +++ | A lot of liquid expressed ++++ | 2-3 fragments) |
| Chitosan-HCl-βGP (pH 6.6)/PRP clot2-2 (1000 U/ml) | Firm and elastic ++++ | Some liquid expressed ++ | Break into 2-3 fragments but still connected |
| Chitosan-HCl-βGP (pH 6.6)/PRP clot2-3 (1000 U/ml) | Firm and elastic ++++ | Almost no liquid expressed + | Break into 2 fragments but still connected |

7—Histological Treatment and Homogeneity Evaluation of PRP/Chitosan Clots

Fixed clots were sectioned in 2 parts. One part was paraffin embedded, stained with Safranin O/Fast Green and observed by optical microscopy. All the photos were taken from the PRP/chitosan clot samples fixed 60 minutes after the clots were prepared, two photos taken with the 5× and 40× objectives from different regions of each sample were used for homogeneity evaluation. Each specimen was observed under microscopy with special emphasis on: presence of bubbles or cracks; presence and distribution of precipitates of chitosan described as: large aggregates or small aggregates; chitosan distribution and whether or not they are homogeneously dispersed across the section; erythrocyte morphology in term of discoid, shrunken, swollen or chaining.

The homogeneity (average value) of clot 2 (2 of 3 samples were "±") made by mixing PRP with chitosan-HCl-βGP (pH 6.6) was slightly better than clot 1 made by mixing PRP with chitosan-HCl—NaCl (pH 6.6) (1 of 3 samples was "±"). The homogeneity of the clots prepared with mixing method 3 was better (2 of 2 samples were "±") than the homogeneity of clots prepared with mixing method 2 (1 sample was "±", 1 sample was "−") or mixing method 1 (both samples were "−"). There were a lot of bubbles in the clots prepared with mixing method 1 and less bubbles in clots prepared with mixing method 2 and mixing method 3. These results showed that mixing method 1 is not ideal to prepare homogenous PRP/chitosan clots with thrombin/CaCl$_2$ activation, the best mixing method was mixing method 3 (Table 4).

TABLE 4

Homogeneity of PRP/chitosan clots.

| Clot-1 sample (with NaCl) | Homogeneity of clot-1 | Clot-2 sample (with βGP) | Homogeneity of clot-2 |
|---|---|---|---|
| PRP1-1 (mixing method 1) | − | PRP2-1 (mixing method 1) | − |
| PRP1-2 (mixing method 2) | − | PRP2-2 (mixing method 2) | ± |

TABLE 4-continued

Homogeneity of PRP/chitosan clots.

| Clot-1 sample (with NaCl) | Homogeneity of clot-1 | Clot-2 sample (with βGP) | Homogeneity of clot-2 |
|---|---|---|---|
| PRP1-3 (mixing method 3) | ± | PRP2-3 (mixing method 3) | ± |

EXAMPLE 2

Runniness Test and Coagulation Time Test for PRP/Chitosan Mixtures without any Activators (No Thrombin or Calcium) by Using Different Mix Ratios 1—Preparation of Chitosan (1.62% w/w)-HCl (38 mM)-NaCl (160 mM) Solution; without NaOH, pH: 6.6; Total Volume: 10.0 ml The chitosan-HCl—NaCl solution was prepared with chitosan $M_n$ 232 kDa, 81% DDA as described hereinabove. The pH of the chitosan solution was physiological at 6.6 and the osmolality was also physiological (359 mOsm/kg; Table 5).

2—Preparation of Chitosan (1.62% w/w)-HCl (71 mM)-βGP (2.15%) Solution, pH: 6.6, Total Volume: 9.0 ml The chitosan-HCl-βGP solution was prepared with chitosan $M_n$ 232 kDa, 81% DDA as described hereinabove. The pH of the chitosan solution was physiological at 6.6 and the osmolality was also physiological (352 mOsm/kg; Table 5).

TABLE 5

Composition and properties of chitosan solutions.

| Solution No and type. | $C_{chitosan}$ (% w/w) | $C_{HCl}$ (mM) | $C_{NaCl}$ (mM) | $C_{\beta GP}$ (% w/w) | Precipitation | pH (Measured) | Osmolality (mOsm/kg) |
|---|---|---|---|---|---|---|---|
| 1. Chitosan-HCl—NaCl pH 6.6 | 1.62 | 38 | 160 | no | no | 6.57 | 359 |
| 2. Chitosan-HCl-βGP pH 6.6 | 1.62 | 71 | no | 2.15 | no | 6.63 | 352 |

3—Drawing Blood

Blood was extracted from rabbits using sterile technique, started by injecting 0.3 cc/kg Hypnorm® IM to the rabbits (for example 0.9 cc for a 3 kg rabbit). First, for each rabbit, ~2 ml of blood was collected in a Vacutainer® tube containing EDTA (Fisher, BD, Product No 02-683-99A) to obtain CBC (complete blood count) and platelet count. Second, for each rabbit, ~26 ml of blood was collected in 3 Vacutainer® tubes containing ACD (VWR, BD, Product No VT4606) to prepare anti-coagulate whole blood and PRP. Each Vacutainer® tube can contain up to 8.5 ml blood. Two rabbit were used in this experiment.

4—Isolating PRP from Anti-Coagulated Whole Blood

PRP was isolated from rabbit whole blood by differential centrifugation as described hereinabove. About 4.5 ml PRP can be harvested from the ACD blood collected from each rabbit.

5—Experiment Part 1: Runniness Test of PRP/Chitosan Mixture

To prepare the PRP/chitosan-HCl—NaCl (pH 6.6) (mix ratios 3:1 v/v), 0.9 ml of platelet-rich plasma (PRP) was pipetted into cryotubes containing 300 µl chitosan-HCl—NaCl (pH 6.6) solution and three 0.39 g stainless steel balls, mixed by hand for 10 seconds (the tube shaken and reversed about 50 times vigorously). To prepare the PRP/chitosan-HCl—NaCl (pH 6.6) mixture (mix ratio 2:1 v/v), 0.8 ml of platelet-rich plasma (PRP) was pipetted into cryotubes containing 400 µl chitosan-HCl—NaCl (pH 6.6) solution and three 0.39 g stainless steel balls, mixed by hand for 10 seconds (the tube shaken and reversed about 50 times vigorously). To prepare the PRP/chitosan-HCl-βGP (pH 6.6) mixture (mix ratio: 3:1 and 2:1 v/v), all procedures described hereinabove were repeated by mixing PRP with chitosan-HCl-βGP (pH 6.6) solution.

For the runniness test, a total of 5 samples were tested: Samples 1 and 2 were PRP/chitosan-HCl—NaCl (pH 6.6) mixtures at mix ratio 3:1 and 2:1 v/v; Samples 3 and 4 were PRP/chitosan-HCl-βGP (pH 6.6) mixtures at mix ratio 3:1 and 2:1 v/v, Samples 5 was PRP without chitosan as a control. A clean plastic board was tilted on the bench top in an angle of about 45°. About 0.5 ml mixture from each sample was pipetted, then three drops of each sample were placed carefully onto the surface of the board (the distance between each sample was about 2 cm), the runniness of the mixtures was observed and photos taken at 30 seconds, 1 minute, 2 minutes, 3 minutes, 5 minutes and 10 minutes.

Figure 5:
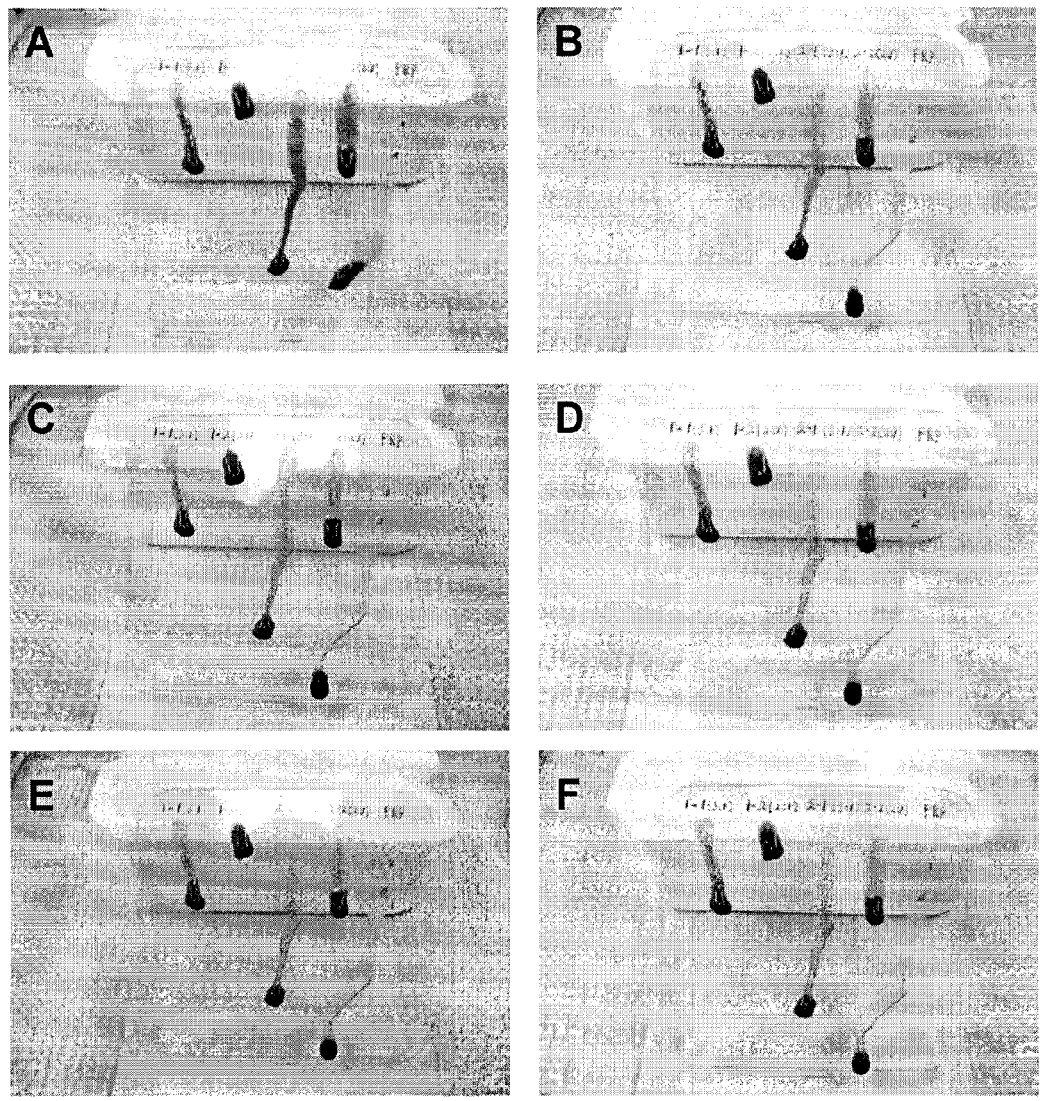
FIG. 5 corresponds to photographic representations of runniness tests of non-activated PRP/chitosan mixtures to evaluate handling properties at different times after mixing (A: 30 seconds; B: 1 min.; C: 2 min.; D: 3 min.; E: 5 min.; and F: 10 min.); wherein the sample numbers are from left to right: 1-1 (with NaCl, mix ratio: 3:1); 1-2 (with NaCl, mix ratio: 2:1); 2-1 (with βGP, mix ratio: 3:1); 2-2 (with βGP, mix ratio: 2:1); Control (pure PRP).

The runniness test results (FIG. 5) showed that pure PRP demonstrated very liquid properties by flowing almost throughout the plastic board in 1 minute, the running distance of different samples were different, and the running distance didn't change significantly from 30 seconds to 10 minutes. For the same mix ratio, the running distance of PRP/chitosan-NaCl was much shorter than PRP/chitosan-βGP, possibly because the chitosan solution with NaCl was more viscous than chitosan solution with βGP and the chitosan solution with NaCl coagulates faster than the chitosan solution with βGP. For the same chitosan solution, the running distance of mix ratio 3:1 v/v was much longer than mix ratio 2:1 v/v. These results suggest that the use of higher chitosan concentrations (2%) and greater ratio of chitosan solution to PRP resulted in more attractive handling properties since these mixtures were more paste-like and more viscous and thus easier to apply in cartilage defects and to other sites that are challenging for delivery.

6—Experiment Part 2: Preparing PRP/Chitosan Clots and Measuring the Coagulation Time and Mechanical Strength of the Clots To prepare the PRP/chitosan-HCl—NaCl (pH6.6) and PRP/chitosan-HCl-βGP (pH 6.6) mixtures (mix ratios 3:1 and 2:1 v/v), the same preparation procedures described hereinabove were followed. For each mixture, 300 µl was transferred into 3 glass tubes at 37° C. with a 1 ml syringe to prepare three clots: 1 clot was used to test coagulation time and fixed immediately after it coagulated, 1 clot was used to test coagulation time and fixed after 60 minutes, 1 clot was used to test coagulation time mechanical strength after 60 minutes. Coagulation of the clot was determined by visualization of the clot at 37° C. as described hereinabove. Mechanical strength was tested as described hereinabove.

Figure 6:
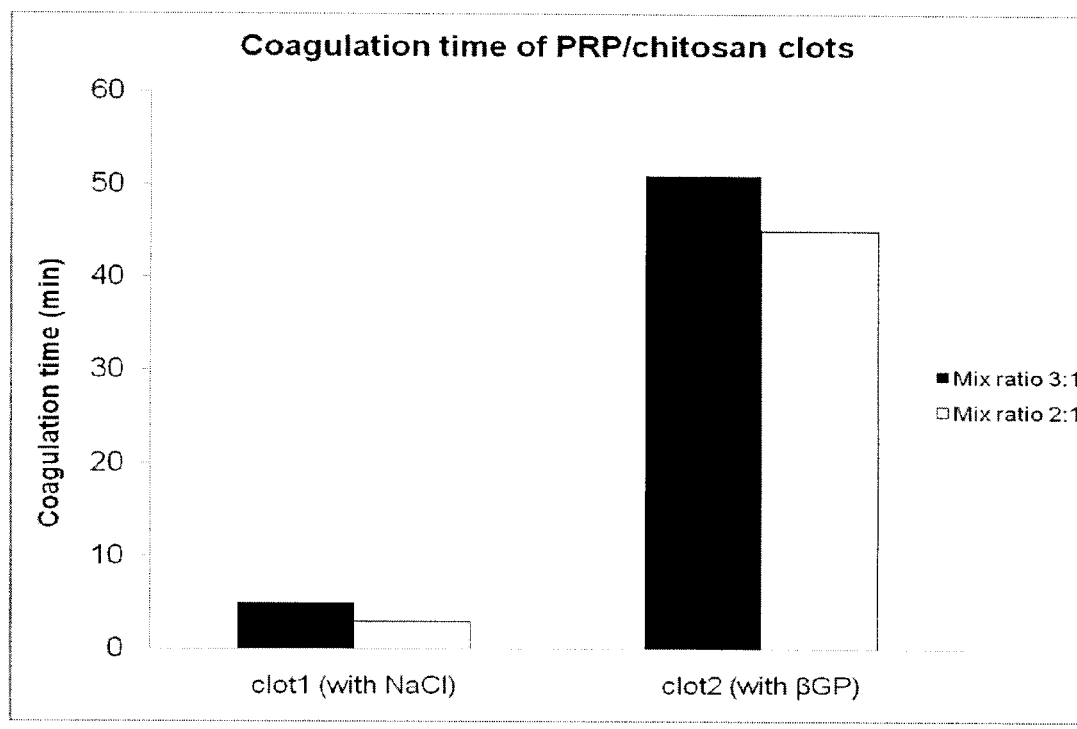
FIG. 6 is a histogram reflecting the coagulation time of non-activated PRP/chitosan mixtures (PRP/chitosan-HCl—NaCl pH 6.6 or PRP/chitosan-HCl-βGP pH 6.6) with different mix ratios.

Coagulation test results (Table 6 and FIG. 6) showed that PRP/chitosan mixtures with NaCl coagulated within 5 minutes (5 minutes for mix ratio 3:1 vs 3 minutes for mix ratio 2:1). PRP/chitosan mixtures with βGP coagulated after 45 minutes (51 minutes for mix ratio 3:1 vs 45 minutes for mix ratio 2:1). For both mix ratios (3:1 and 2:1), the mixtures with NaCl (clot1) coagulated much faster than the mixture with βGP (clot2). Clots prepared with a mix ratio 2:1 coagulated slightly faster than clots prepared with a mix ratio 3:1, suggesting that increasing chitosan concentration accelerated the coagulation or created a more viscous solution.

Figure 7:
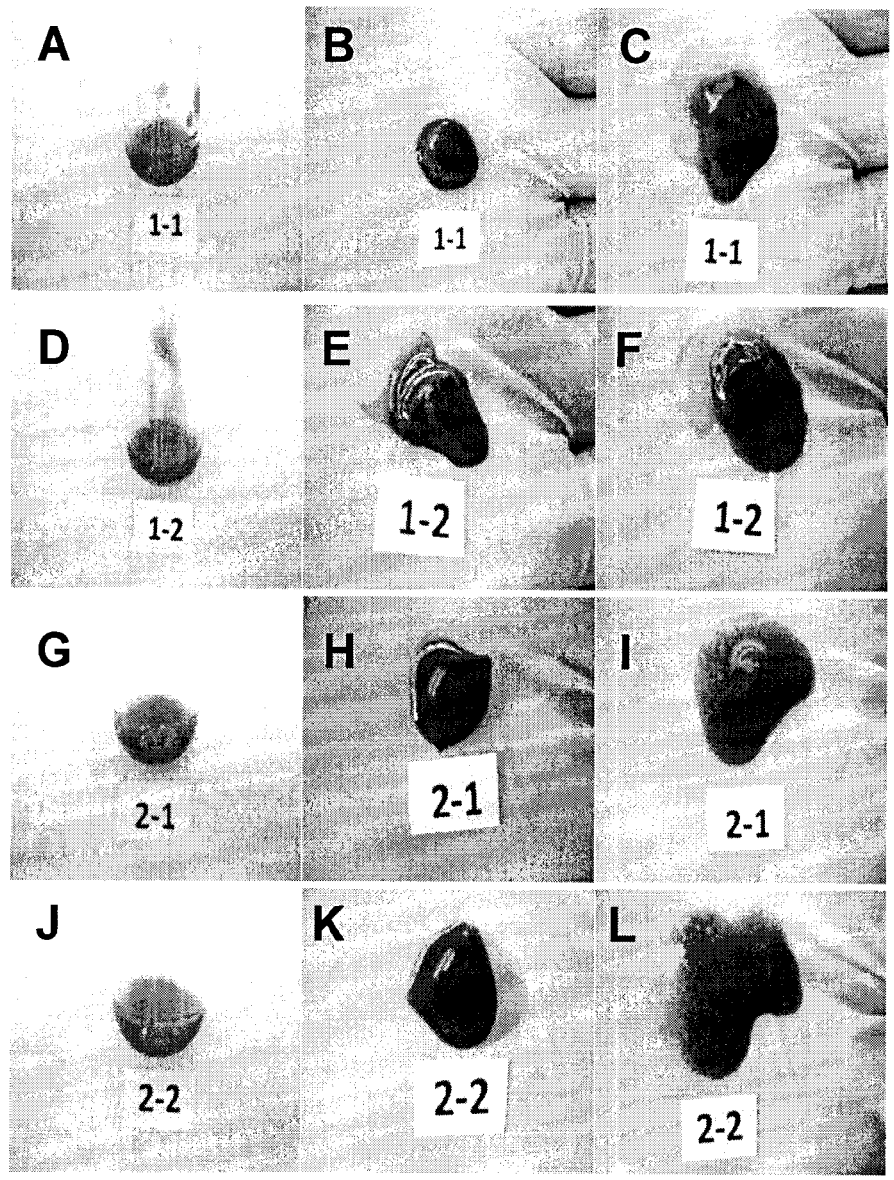
FIG. 7 corresponds to photographic representations of non-activated PRP/chitosan clots with different mix ratios in the glass tubes (A, D, G, J), after removal from the tubes (B, E, H, K) and after mechanical strength test (C, F, I, L) wherein the sample numbers are: 1-1 (with NaCl, mix ratio 3:1); 1-2 (with NaCl, mix ratio 2:1); 2-1 (with βGP, mix ratio 3:1); 2-2 (with βGP, mix ratio 2:1).
Figure 8:
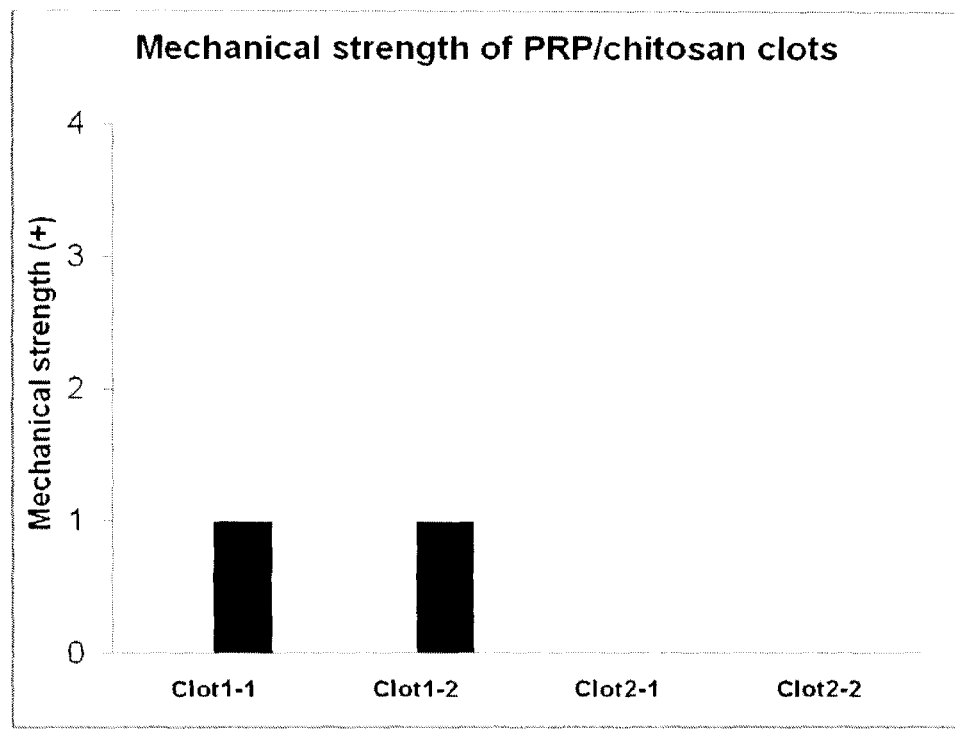
FIG. 8 is a histogram reflecting the mechanical strength of non-activated PRP/chitosan clots wherein the sample numbers are: 1-1 (with NaCl, mix ratio: 3:1); 1-2 (with NaCl, mix ratio: 2:1); 2-1 (with βGP, mix ratio: 3:1); 2-2 (with βGP, mix ratio: 2:1).

With regard to the mechanical strength of clots (Table 7, FIGS. 7 and 8), the two clots with NaCl were not firm and were easily broken. Following crushing, the clots were flattened, the mechanical strength of the clots were close to "+" (between 0 and +). The two clots with (GP) were gel-like mixtures. After they were poured out of the tubes, they looked like viscous mud (very fragile), and the mechanical strengths of the clots were "0". The mechanical strengths of PRP clots prepared without activation by thrombin and $CaCl_2$ (just mix PRP with chitosan) was much weaker than the PRP clots with thrombin and $CaCl_2$ in vitro (See Table 3 for the mechanical properties with thrombin and Table 11 for mechanical properties with $CaCl_2$).

7—Histological Treatment and Homogeneity Evaluation of PRP/Chitosan Clots

Histological treatment and homogeneity evaluation was performed as described hereinabove.

The histology results (Table 8) showed that the PRP/chitosan clots prepared with NaCl were homogenous, both mix ratios were "+". The homogeneity of the PRP/chitosan clots prepared with βGP was poor, both mix ratios were "−". There was more chitosan observed in the clots prepared with a mix ratio of 2:1 v/v than the clots prepared with a mix ratio of 3:1 v/v.

TABLE 8

Homogeneity of PRP/chitosan clots prepared with NaCl or βGP at mix ratios 3:1 or 2:1.

| Clot-1 samples (with NaCl) | Homogeneity of clot-1 | Clot-2 samples (with βGP) | Homogeneity of clot-2 |
|---|---|---|---|
| PRP 1-1-2-60 (3:1) | + | PRP 2-1-2-60 (3:1) | − |
| PRP 1-2-2-60 (2:1) | + | PRP 2-2-2-60 (2:1) | − |

TABLE 6

Coagulation time of PRP/chitosan mixtures.

| Mixture | Mixing ratio and sample number | | Coagulation time (Min) | Mean value (Min) | Comments |
|---|---|---|---|---|---|
| PRP/chitosan-HCl—NaCl pH 6.6 (clot1) | 3:1 | 1 | 5 | 5 | For clot1 (with NaCl), both mix ratios (3:1 and 2:1) coagulated within 5 minutes (5 min for 3:1 and 3 min for 2:1); after 60 minutes, the clot didn't retract and didn't express serum. For clot2 (with βGP), both mix ratios (3:1 and 2:1) coagulated after 45 minutes (51 min for 3:1 and 45 min for 2:1), and formed gel-like clots (fragile); after 60 minutes, the clot didn't retract and didn't express serum. The coagulation times of mix ratio 2:1 were less than the coagulation time of mix ratio 3:1 in mixtures with NaCl and βGP. |
| | | 2 | 5 | | |
| | | 3 | 5 | | |
| | 2:1 | 1 | 3 | 3 | |
| | | 2 | 3 | | |
| | | 3 | 3 | | |
| PRP/chitosan-HCl-βGP pH 6.6 (clot2) | 3:1 | 1 | 51 | 51 | |
| | | 2 | 51 | | |
| | | 3 | 51 | | |
| | 2:1 | 1 | 45 | 45 | |
| | | 2 | 45 | | |
| | | 3 | 45 | | |

TABLE 7

Mechanical strength test of PRP/chitosan clots prepared without any activators (no thrombin, no calcium).

| Sample | Resistance to compression | Liquid expressed | Crushed appearance |
|---|---|---|---|
| PRP/Chitosan-HCl—NaCl (pH 6.6) clot1-1 (3:1) | Easily broken Close to "+" | Almost no liquid expressed + | Flattened |
| PRP/Chitosan-HCl—NaCl (pH 6.6) clot1-2 (2:1) | Easily broken Close to "+" | Almost no liquid expressed + | Flattened |
| PRP/Chitosan-HCl-βGP (pH6.6) clot2-1 (3:1) | Viscous mud Close to "0" | Almost no liquid expressed + | Flattened |
| PRP/Chitosan-HCl-βGP (pH 6.6) clot2-1 (2:1) | Viscous mud Close to "0" | Almost no liquid expressed + | Flattened |

EXAMPLE 3

Preparation of PRP/chitosan Clots by using 1.62% and 2.0% Chitosan Solutions at Mix Ratios of 2:1 and 3:1 and with a Small Volume of $CaCl_2$ Solution as Activator 1—Preparation of Chitosan (1.62% w/w)-HCl (38 mM)-NaCl (160 mM) Solution; without NaOH, pH: 6.6; Total Volume: 10.0 ml The chitosan-HCl—NaCl solution was prepared with chitosan $M_n$ 232 kDa, 81% DDA as described hereinabove. The pH of the chitosan solution was physiological at 6.6 and the osmolality was also physiological (344 mOsm/kg; Table 9).

2—Preparation of Chitosan (2.0% w/w)-HCl (50 mM)-NaCl (150 mM) Solution; pH: 6.5; Total Volume: 10.0 ml 0.222 g of chitosan ($M_n$ 232 kDa, 81% DDA) was weighed in a 20 ml beaker, $H_2O$dd added to the beaker, until the weight of chitosan+H$_2$O=9.20 g. A magnetic stir bar was inserted into the beaker; the solution stirred for about 10 minutes in order to hydrate the chitosan powder as much as possible. 0.50 ml of HCl 1 N (Sigma, Product No 318949) was added to the solution under moderate stirring. The beaker was covered with Parafilm™, and the solution heated to about 60° C. for 4 hours, stirred overnight until completely dissolved. 0.30 ml of 5N NaCl (Sigma, Product No S-9888) solution was added into the beaker and well mixed. The pH of the chitosan solution was physiological at 6.5 and the osmolality was also physiological (324 mOsm/kg; Table 9).

TABLE 9

Composition and properties of chitosan solutions

| Solution No and type. | $C_{chitosan}$ (% w/w) | $C_{HCl}$ (mM) | $C_{NaCl}$ (mM) | $C_{\beta GP}$ (% w/w) | Precipitation | pH (Measured) | Osmolality (mOsm/kg) |
|---|---|---|---|---|---|---|---|
| 1. Chitosan-HCl—NaCl pH 6.6 | 1.62 | 38 | 160 | no | no | 6.56 | 344 |
| 2. Chitosan-HCl—NaCl pH 6.5 | 2.0 | 50 | 150 | no | no | 6.49 | 324 |

Two different chitosan solutions (with NaCl, 1.62% and 2.0%) with similar physiological osmolality were successfully prepared. Chitosan solution 1 with higher concentration (2.0%) was much more viscous than chitosan solution 2 with lower concentration (1.62%) by visualization.

3—Drawing Blood

Blood was extracted from rabbits using sterile technique as described previously. Two rabbits were used in this experiment.

4—Isolating PRP from Anti-Coagulated Whole Blood

PRP was isolated from rabbit whole blood by differential centrifugation as described previously. About 4.5 ml PRP can be harvested from the ACD blood collected from each rabbit and about 9.0 ml PRP was harvested in this experiment.

5—Preparing CaCl$_2$ Activator Solutions

To prepare the 1.3% (w/w) and 3% (w/w) CaCl$_2$ solution, respectively 0.26 g and 0.60 g of CaCl$_2$.2H$_2$O (Sigma, Product No C7902-500G) were weighed and deposited in two different 50 ml beakers, H$_2$Odd was added into these beakers, until the weight of CaCl$_2$.2H$_2$O+H$_2$O=15 g. A magnetic stir bar was inserted into the beakers and stirred until completely dissolved.

6—Preparing PRP/Chitosan Clots and Measuring the Coagulation Time and Mechanical Strength of the Clots PRP/chitosan-HCl—NaCl mixtures were prepared at mix ratio 3:1 v/v: 0.9 mL of platelet-rich plasma (PRP) was pipetted into cryotubes containing 300 µl 1.62% chitosan-HCl—NaCl (pH 6.6) solution and three 0.39 g stainless steel balls, mixed by hand for 10 seconds (the tube was shaken and reversed about 50 times vigorously). 300 µl was transferred into 3 glass tubes at 37° C. with a 1 ml syringe. Immediately 60 µL 1.3% (w/w) calcium chloride solution was instilled very carefully and slowly on the surface of PRP/chitosan mixture of each glass tube to prepare 3 clots: 1 clot was used to test coagulation time and fixed immediately after it coagulated, 1 clot was used to test coagulation time and fixed after 60 minutes, 1 clot was used to test coagulation time and mechanical strength after 60 minutes.

All procedures which are described hereinabove were repeated with 2.0% chitosan-HCl—NaCl (pH 6.5) solution instead of using 1.62% chitosan solution.

PRP/chitosan-HCl—NaCl mixtures were prepared at mix ratio 2:1 v/v: 0.8 ml of platelet-rich plasma (PRP) was pipetted into the cryotubes containing 400 µl 1.62% chitosan-HCl—NaCl (pH 6.6) solution and three 0.39 g stainless steel balls, mixed by hand for 10 seconds (the tube was shaken and reversed about 50 times vigorously). 300 µl was transferred into 3 glass tubes at 37° C. with a 1 ml syringe. Immediately 60 µL 1.3% (w/w) calcium chloride solution was instilled very carefully and slowly on the surface of PRP/chitosan mixture of each glass tube to prepare 3 clots: 1 clot was used to test coagulation time and fixed immediately after it coagulated, 1 clot was used to test coagulation time and fixed after 60 minutes, 1 clot was used was used to test and mechanical strength after 60 minutes. All procedures which described hereinabove were repeated with a 2.0% chitosan-HCl—NaCl (pH 6.5) solution.

The PRP/chitosan mixtures were also activated with a 3% w/w CaCl$_2$ solution. All procedures described hereinabove were repeated with a 3% w/w CaCl$_2$ solution instead of a 1.3% w/w CaCl$_2$ solution.

Coagulation of the clot was determined by visualization of the clot at 37° C. as described hereinabove. Mechanical strength was tested as described hereinabove. The coagulation test results (see Table 10 and FIG. 9) showed that all the mixtures coagulated within 8 minutes. For the mixtures activated by 1.3% CaCl$_2$, PRP mixed with 1.62% chitosan at mix ratio 3:1 coagulated at 8 minutes, PRP mixed with 2.0% chitosan at mix ratio 3:1 coagulated at 6 minutes, PRP mixed with 1.62% chitosan at mix ratio 2:1 coagulated at 7 minutes, PRP mixed with 2.0% chitosan at mix ratio 2:1 coagulated at 5 minutes. For the mixtures activated by 3% CaCl$_2$, PRP mixed with 1.62% chitosan at mix ratio 3:1 coagulated at 8 minutes, PRP mixed with 2.0% chitosan at mix ratio 3:1 coagulated at 5 minutes, PRP mixed with 1.62% chitosan at mix ratio 2:1 coagulated at 5 minutes, PRP mixed with 2.0% chitosan at mix ratio of 2:1 coagulated at 3 minutes. For the same mix ratio, a more concentrated chitosan solution needed less time to clot (2.0% w/w<1.62% w/w). For the same chitosan concentration, PRP mixed with more chitosan solution needed less time to clot (mix ratio of 2:1 v/v<mix ratio of 3:1 v/v). PRP/chitosan mixtures activated with 3% CaCl$_2$ solution coagulated slightly faster than the mixtures activated with 1.3% w/w CaCl$_2$ solution (3 of 4 samples coagulated faster with 3% w/w CaCl$_2$).

TABLE 10

Coagulation time of PRP/chitosan mixtures

| Mixture | Chitosan concentration and mix ratios of PRP to chitosan | | Coagulation time (Min) | Mean value (Min) | Comments |
|---|---|---|---|---|---|
| PRP/chitosan-HCl—NaCl (clot1: adding 1.3% CaCl$_2$ solution as activator) | 1.62% and 3:1 (clot1-1) | 1<br>2<br>3 | 8<br>8<br>8 | 8 | All the mixtures activated by 1.3% CaCl$_2$ coagulated within 8 minutes; for same mix ratio, more concentrated chitosan solution needed shorter time to form a clot (2.0% < 1.62%). For same chitosan solution, PRP mixed with more chitosan solution need shorter time to form a clot (mix ratio of 2:1 < mix ratio of 3:1). |
| | 2.0% and 3:1 (clot1-2) | 1<br>2<br>3 | 6<br>6<br>6 | 6 | |
| | 1.62% and 2:1 (clot1-3) | 1<br>2<br>3 | 7<br>7<br>7 | 7 | |
| | 2.0% and 2:1 (clot1-4) | 1<br>2<br>3 | 5<br>5<br>5 | 5 | |
| PRP/chitosan-HCl—NaCl (clot2: adding 3% CaCl$_2$ solution as activator) | 1.62% and 3:1 (clot2-1) | 1<br>2<br>3 | 8<br>8<br>8 | 8 | All the mixtures activated by 3% CaCl$_2$ coagulated within 8 minutes; for same mix ratio, more concentrated chitosan solution needed shorter time to form a clot (2.0% < 1.62%). For same chitosan solution, PRP mixed with more chitosan solution need shorter time to form a clot (mix ratio of 2:1 < mix ratio of 3:1). |
| | 2.0% and 3:1 (clot2-2) | 1<br>2<br>3 | 5<br>5<br>5 | 5 | |
| | 1.62% and 2:1 (clot2-3) | 1<br>2<br>3 | 5<br>5<br>5 | 5 | |
| | 2.0% and 2:1 (clot2-4) | 1<br>2<br>3 | 3<br>3<br>3 | 3 | |

TABLE 11

Mechanical strength test of PRP/chitosan clots.

| Sample | Resistance to compression | Liquid expressed | Crushed appearance |
|---|---|---|---|
| Chitosan-HCl—NaCl/PRP clot1-1 (1.62%, 3:1, 1.3% CaCl$_2$) | Firm and elastic ++++ | ++ | 2 fragments but still connected |
| Chitosan-HCl—NaCl/PRP clot1-2 (2.0%, 3:1, 1.3% CaCl$_2$) | Firm and elastic ++++ | + | 2 fragments |
| Chitosan-HCl—NaCl/PRP clot1-3 (1.62%, 2:1, 1.3% CaCl$_2$) | Firm and elastic ++++ | ++ | 2 fragments but still connected |
| Chitosan-HCl—NaCl/PRP clot1-4 (2.0%, 2:1, 1.3% CaCl$_2$) | Firm and elastic ++++ | ++ | 2 fragments but still connected |
| Chitosan-HCl—NaCl/PRP clot2-1 (1.62%, 3:1, 3% CaCl$_2$) | Firm and elastic ++++ | ++ | 2 fragments but still connected |
| Chitosan-HCl—NaCl/PRP clot2-2 (2.0%, 3:1, 3% CaCl$_2$) | Firm and elastic ++++ | + | Hole in center |
| Chitosan-HCl—NaCl/PRP clot2-3 (1.62%, 2:1, 3% CaCl$_2$) | Firm and elastic ++++ | ++ | 2 fragments but still connected |
| Chitosan-HCl—NaCl/PRP clot2-4 (2.0%, 2:1, 3% CaCl$_2$) | Firm and elastic ++++ | + | Hole in center |

When the mechanical strength of clots was tested after 60 minutes, it was found that all eight clots were firm and elastic. For clot1-1 (1.62%, 3:1 and 1.3% CaCl$_2$ solution), some liquid exuded (scored as ++), the clot didn't retract significantly, the mechanical strength was "++++", after crushing, the clot broke in two connected fragments. For clot1-2 (2.0%, 3:1 and 1.3% CaCl$_2$ solution), almost no liquid exuded (scored as +), the clot didn't retract, the mechanical strength was "++++", after crushing, the clot broke in two fragments. For clot1-3 (1.62%, 2:1 and 1.3% CaCl$_2$ solution), some liquid exuded (scored as ++), the clot didn't retract significantly, the mechanical strength was "++++", after crushing, the clot broke in two connected fragments. For clot1-4 (2.0%, 2:1 and 1.3% CaCl$_2$ solution), some liquid exuded (scored as ++), the clot didn't retract significantly, the mechanical strength was "++++", after crushing, the clot broke in two connected fragments. For clot2-1 (1.62%, 3:1 and 3% CaCl$_2$ solution), some liquid exuded (scored as ++), the clot didn't retract significantly, the mechanical strength was "++++", after crushing, the clot broke in two connected fragments. For clot2-2 (2.0%, 3:1 and 3% CaCl$_2$ solution), a little liquid exuded (scored as +), the clot didn't retract significantly, the mechanical strength was "++++", after crushing, the clot had just a hole in centre. For clot2-3 (1.62%, 2:1 and 3% CaCl$_2$ solution), some liquid exuded (scored as ++), the clot didn't retract significantly, the mechanical strength was "++++", after crushing, the clot broke in two connected fragments. For clot2-4 (2.0%, 2:1 and 3% CaCl$_2$ solution), almost no liquid exuded (scored as +), the clot didn't retract, the mechanical strength was "++++", after crushing, the clot had just a hole in center (Table 11, FIG. 10).

In this experiment (Table 11 and FIG. 10), all eight clots didn't retract significantly, but from the amount of liquid expressed and the photos of clots before crushing, the retraction of clots with 2% w/w chitosan was less than the clots with 1.62% w/w chitosan. Although the mechanical strength test showed identical scored for all clots, it appeared that the mechanical strength of clots prepared with 2% w/w chitosan was slightly better (after crushing, 2 of 4 samples had just a hole in the center of clots, 1 of 4 sample was broken into two connected fragments and 1 of 4 samples was broke into two fragments) than the clots prepared with 1.62% w/w chitosan (after crushing, 4 of 4 samples were broken into two connected fragments).

7—Histological Treatment and Homogeneity Evaluation of PRP/Chitosan Clots

Histological treatment and homogeneity evaluation was performed as described hereinabove.

The histological evaluation results (Table 12) showed that the homogeneity of all eight clots was satisfactory (none of them was −, all were above ±). For clot1-1 (1.62%, 3:1, 1.3% CaCl$_2$), homogeneity was +; for clot1-2 (2.0%, 3:1, 1.3% CaCl$_2$), homogeneity was +; for clot1-3 (1.62%, 2:1, 1.3% CaCl$_2$), homogeneity was +; for clot1-4 (2.0%, 2:1, 1.3% CaCl$_2$), omogeneity was +(between ± and +); For clot2-1 (1.62%, 3:1, 3% CaCl$_2$), homogeneity of clot +(between ± and +); for clot2-2 (2.0%, 3:1, 3% CaCl$_2$), homogeneity was +(between ± and +); for clot2-3 (1.62%, 2:1, 3% CaCl$_2$), homogeneity of clot +(between ± and +); for clot2-4 (2.0%, 2:1, 3% CaCl$_2$), homogeneity was +.

The homogeneity of clots prepared with 1.3% w/w CaCl$_2$ solution (3 of 4 samples were +, 1 of 4 samples was between ± and +) was better than the clots prepared with 3% w/w CaCl$_2$ solution (1 of 4 were samples was +, 3 of 4 samples were between ± and +).

TABLE 12

Homogeneity of PRP/chitosan clots

| Clot samples (with NaCl) | Homogeneity of clot |
|---|---|
| PRP 1-1-60 (1.62%, 3:1, 1.3% CaCl$_2$) | + |
| PRP 1-2-60 (2.0%, 3:1, 1.3% CaCl$_2$) | + |
| PRP 1-3-60 (1.62%, 2:1, 1.3% CaCl$_2$) | + |
| PRP 1-4-60 (2.0%, 2:1, 1.3% CaCl$_2$) | + (between ± and +) |
| PRP 2-1-60 (1.62%, 3:1, 3% CaCl$_2$) | + (between ± and +) |
| PRP 2-2-60 (2.0%, 3:1, 3% CaCl$_2$) | + (between ± and +) |
| PRP 2-3-60 (1.62%, 2:1, 3% CaCl$_2$) | + (between ± and +) |
| PRP 2-4-60 (2.0%, 2:1, 3% CaCl$_2$) | + |

EXAMPLE 4

Formulation and Characterization of PRP/Chitosan Clots Prepared with Chitosan Solutions of Different Molecular Weight (Rabbit Blood) and an Inversion Mixing Method 1—Preparation of Chitosan (1.62% w/w)-HCl (38 mM)-NaCl (160 mM) Solution; without NaOH, pH: 6.6; Total Volume: 10.0 ml The chitosan-HCl—NaCl solutions were prepared with chitosan $M_n$ 232 kDa, 81% DDA or with chitosan $M_n$ 298 kDa, 76% DDA as described hereinabove. The pH of the chitosan solutions were physiological at 6.6 and 6.5 and the osmolality was also physiological (332 and 330 mOsm/kg; Table 13).

2—Preparation of Chitosan (1.62% w/w)-HCl (71 mM)-βGP (2.15%) solution, pH: 6.6, Total Volume: 9.0 ml (Respectively using Chitosan CH1007028, CH0050602A)

The chitosan-HCl-βGP solutions were prepared with chitosan $M_n$ 232 kDa, 81% DDA or with chitosan $M_n$ 298 kDa, 76% DDA as described hereinabove. The pH of the chitosan solutions were physiological at 6.7 and the osmolality was also physiological (341 and 339 mOsm/kg; Table 13).

TABLE 13

Composition and properties of chitosan solutions.

| Solution No and type. | $C_{chitosan}$ (% w/w) | $C_{HCl}$ (mM) | $C_{NaCl}$ (mM) | $C_{\beta GP}$ (% w/w) | Precipitation | pH (Measured) | Osmolality (mOsm) |
|---|---|---|---|---|---|---|---|
| 1-1. Chitosan-HCl—NaCl pH6.6(CH0100702B) | 1.62 | 38 | 160 | no | no | 6.61 | 332 |
| 1-2. Chitosan-HCl-βGP pH6.6(CH0100702B) | 1.62 | 71 | No | 2.15 | no | 6.67 | 341 |
| 2-1. Chitosan-HCl—NaCl pH6.6(CH0050602A) | 1.62 | 38 | 160 | no | no | 6.52 | 330 |
| 2-2. Chitosan-HCl-βGP pH6.6(CH0050602A) | 1.62 | 71 | No | 2.15 | no | 6.65 | 339 |

3—Drawing Blood

Blood was extracted from rabbits using sterile technique, as described hereinabove. One rabbit was used in this experiment.

4—Isolating PRP from Anti-Coagulated Whole Blood

PRP was isolated from rabbit whole blood by differential centrifugation as described hereinabove. About 4.5 ml PRP was harvested from the ACD blood collected the rabbit.

5—Experiment Part 1: Formulation and Characterization of PRP/1.62% Chitosan Clots (with NaCl and βGP)

PRP/chitosan-HCl—NaCl mixtures were prepared at mix ratio 3:1 v/v: 0.9 mL of platelet-rich plasma (PRP) was pipetted into cryotubes containing 300 μl 1.62% w/w chitosan-HCl—NaCl (pH 6.6) solution and three 0.39 g stainless steel balls, mixed by hand for 10 seconds (the tube was shaken and reversed about 50 times vigorously). 240 μL 3% w/w CaCl$_2$ solution was added to the PRP/chitosan mixture and mixed gently by inverting the tube 5 times in 5 seconds. 300 μL of each mixture was transferred into three glass tubes to prepare 3 clots: 1 clot was used to test coagulation time and fixed immediately after it coagulated, 1 clot was used to test coagulation time and fixed after 60 minutes, 1 clot was used to test coagulation time and mechanical strength after 60 minutes. All the procedures described hereinabove were repeated by mixing PRP with 1.62% w/w chitosan-HCl-βGP (pH6.6) solution instead of 1.62% w/w chitosan-HCl—NaCl (pH6.6) solution. All procedures which are described hereinabove were performed with the 2 different chitosans: chitosan CH0100702B ($M_n$ 232 kDa, 81% DDA) and chitosan CH0050602A ($M_n$ 298 kDa, 76% DDA).

Coagulation of the clot was determined by visualization of the clot at 37° C. as described hereinabove. Mechanical strength was tested as described hereinabove.

Results showed that all the mixtures prepared with chitosan CH0100702B ($M_n$ 232 kDa, 81% DDA) coagulated within 8 minutes. The coagulation time of PRP/chitosan-HCl—NaCl clots was near equal to the coagulation time of PRP/chitosan-HCl-βGP clots (average was 7.3 minutes versus 7 minutes respectively) (Table 14 and FIG. 11). Results showed that all the mixtures prepared with chitosan CH0050602A ($M_n$ 298 kDa, 76% DDA) coagulated within 8 minutes. The coagulation time of PRP/chitosan-HCl—NaCl clots was near equal to the coagulation time of PRP/chitosan-HCl-βGP clots (average was 7 minutes versus 8 minutes respectively) (Table 14 and FIG. 11).

TABLE 14

Coagulation time of PRP/chitosan clots prepared by inversion with CH0100702B and CH0050602A chitosans.

| Mixture | Concentration of chitosan solution and mix ratio | | Coagulation time (Min) | Mean value (Min) | Comments |
|---|---|---|---|---|---|
| PRP/Chitosan-HCl—NaCl CH0100702B | 1.62% and 3:1 (clot1-1) | 1<br>2<br>3 | 8<br>7<br>7 | 7.3 | All the mixtures coagulated within 8 minutes (from 7 minutes to 8 minutes). |
| PRP/Chitosan-HCl-βGP CH0100702B | 1.62% and 3:1 (clot1-2) | 1<br>2<br>3 | 7<br>7<br>7 | 7 | All the mixtures coagulated at 7 minutes). |
| PRP/Chitosan-HCl—NaCl CH0050602A | 1.62% and 3:1 (clot2-1) | 1<br>2<br>3 | 7<br>7<br>7 | 7 | All the mixtures coagulated at 7 minutes. |
| PRP/Chitosan-HCl-βGP CH0050602A | 1.62% and 3:1 (clot2-2) | 1<br>2<br>3 | 8<br>8<br>8 | 8 | All the mixtures coagulated at 8 minutes. |
| PRP without chitosan | Without chitosan (clot-C) | 1<br>2<br>3 | 16<br>15<br>15 | 15.3 | All the mixtures coagulated within 16 minutes (from 15 minutes to 16 minutes). |

6—Mechanical Strength Test and Liquid Expression

All the clots prepared by inversion were firm and elastic, the mechanical strength of all the clots was "++++". There was no significant difference in mechanical strength between PRP/chitosan-HCl—NaCl clots and PRP/chitosan-HCl—clots. There was no significant difference in mechanical strength among the clots prepared with the different chitosans as well (Table 15 and FIG. 12). After 60 minutes, the PRP/chitosan clots prepared by inversion with CH0100702B and CH0050602A, both with NaCl or βGP, didn't express any liquid and retract (Table 15, FIGS. 13 & 14), the clots were perfectly intact. Meanwhile, the PRP clot without chitosan expressed a lot of liquid (82.9%) and retracted significantly (Table 15, FIGS. 13 & 14).

TABLE 15

Mechanical strength test of PRP/chitosan clots prepared by inversion.

| Sample | Resistance to compression | Weight of the tube (A) | Weight of tube + clot + serum (B) | Weight of Tube + clot (C) | Liquid expressed = (B − C)/(B − A) × 100 | Crushed appearance | Level of hemolysis |
|---|---|---|---|---|---|---|---|
| PRP/1.62% Chitosan-HCl—NaCl (pH6.6) clot1-1 (3:1, CH0100702B) | ++++ | 7.47 g | 7.86 g | 7.86 g | 0 | 2 fragments but still connected | − |
| PRP/1.62% Chitosan-HCl-βGP (pH6.6) clot1-2 (3:1, CH0100702B) | ++++ | 7.46 g | 7.84 g | 7.84 g | 0 | 2 fragments but still connected | − |
| PRP/1.62% Chitosan-HCl—NaCl (pH6.6) clot2-1 (3:1, CH0050602A) | ++++ | 7.53 g | 7.92 g | 7.92 g | 0 | Hole in center | − |
| PRP/1.62% Chitosan-HCl-βGP (pH6.6) clot2-2 (3:1, CH0050602A) | ++++ | 7.48 g | 7.86 g | 7.86 g | 0 | 2 fragments but still connected | − |
| Pure PRP clot-C (without chitosan) | ++++ | 7.38 g | 7.73 g | 7.44 g | 82.9 | 2 fragments but still connected | + |

8—Histological Treatment and Homogeneity Evaluation of PRP/Chitosan Clots

Histological treatment and homogeneity evaluation was performed as described hereinabove.

The PRP/chitosan clots prepared by inversion with βGP were more homogenous (1 of 2 samples was "+" and one was "±" between ± and +) than the PRP/chitosan clots prepared by inversion with NaCl (both samples were "−") (Table 16).

TABLE 16

Homogeneity of PRP/chitosan clots prepared by inversion

| Clot samples (with NaCl) | Homogeneity of clots (with NaCl) | Clot samples (with βGP) | Homogeneity of clots (with βGP) |
|---|---|---|---|
| PRP 1-1 (CH0100702B) | − | PRP 1-2 (CH0100702B) | + |
| PRP 2-1 (CH0050602A) | − | PRP 2-2 (CH0050602A) | ± (between ± and +) |
| PRP-C (without chitosan) | + | N/A | N/A |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A clot-activated polymer composition comprising:
   a) anti-coagulated platelet-rich plasma (PRP) selected from the group consisting of autologous, allogenic, xenogenic and combinations thereof; and
   b) a chitosan, an acid, NaCl and a clot activator comprising a 3% calcium chloride ($CaCl_2$) solution
   wherein the polymer composition comprises a pH above 6.2 and an osmolality between 300 mOsm/kg and 735 mOsm/kg,
   wherein the polymer composition is substantially free of whole blood and added thrombin,
   wherein the clot-activated polymer composition is prepared by combining said PRP to a chitosan solution at a volume ratio of between 2:1 to 3:1, and wherein said chitosan solution comprises said chitosan and said NaCl.

2. The clot-activated polymer composition of claim 1, wherein the volume ratio is 3:1.

3. The clot-activated polymer composition of claim 1, wherein the volume ratio is 2:1.

4. The clot-activated polymer composition of claim 1, wherein the chitosan is 1%.

5. The clot-activated polymer composition of claim 1, wherein the chitosan is 2%.

6. The clot-activated polymer composition of claim 1, wherein the concentration of $CaCl_2$ in said $CaCl_2$ solution is between 1.0% w/w and 25% w/w.

7. The clot-activated polymer composition of claim 1 wherein the concentration of $CaCl_2$ in said $CaCl_2$ solution is between 1.3% w/w and 3% w/w.

8. The clot-activated polymer composition of claim 1, wherein the osmolality between 342 mOsm/kg and 361 mOsm/kg.

9. The clot-activated polymer composition of claim 1, wherein the polymer composition is prepared with a solution having a chitosan concentration of between 1.0% w/w and 10% w/w.

10. The clot-activated polymer composition of claim 9, wherein the chitosan concentration is between 1.62% w/w and 2% w/w.

11. The clot-activated polymer composition of claim 1, wherein the chitosan has a degree of deacetylation (DDA) between 20% and 100%.

12. The clot-activated polymer composition of claim 11, wherein the DDA is 76% or 81%.

13. The clot-activated polymer composition of claim 1, wherein the chitosan has a number average molecular weight (Mn) ranging from 1 kDa to 10 MDa.

14. The clot-activated polymer composition of claim 13, wherein the Mn is 232 kDa or 298 kDa.

15. The clot-activated polymer composition of claim 1, wherein the acid is a mineral acid, an organic acid, or combinations thereof.

16. The clot-activated polymer composition of claim 15, wherein the mineral acid is hydrochloric acid, acetic acid, nitric acid, phosphoric acid, sulfuric acid, boric acid hydrofluoric acid or hydrobromic acid.

* * * * *